United States Patent
Barry

(10) Patent No.: US 7,452,369 B2
(45) Date of Patent: Nov. 18, 2008

(54) SPINE MICROSURGERY TECHNIQUES, TRAINING AIDS AND IMPLANTS

(76) Inventor: Richard J. Barry, 3906 Solar Hills Dr., Vacaville, CA (US) 95688

(*) Notice: Subject to any disclaimer, the term of this patent is extended or adjusted under 35 U.S.C. 154(b) by 742 days.

(21) Appl. No.: 10/968,860

(22) Filed: Oct. 18, 2004

(65) Prior Publication Data
US 2006/0085068 A1    Apr. 20, 2006

(51) Int. Cl.
*A61B 17/70* (2006.01)
*A61B 17/58* (2006.01)

(52) U.S. Cl. .................... 606/279; 606/249

(58) Field of Classification Search ... 623/17.11–17.16, 623/18.11; 606/247, 279
See application file for complete search history.

(56) References Cited

U.S. PATENT DOCUMENTS

| | | | |
|---|---|---|---|
| D059,314 S | 10/1921 | Winsen | |
| 2,537,070 A | 1/1951 | Longfellow | |
| D222,235 S | 10/1971 | Holiday | |
| D377,095 S | 12/1996 | Michelson | |
| D398,837 S | 9/1998 | Spence | |
| 5,904,719 A * | 5/1999 | Errico et al. | 623/17.16 |
| D412,435 S | 8/1999 | Cultice, Jr. | |
| D424,421 S | 5/2000 | Ono | |
| 6,371,989 B1 * | 4/2002 | Chauvin et al. | 623/17.11 |
| 6,419,704 B1 | 7/2002 | Ferree | |
| 6,485,518 B1 * | 11/2002 | Cornwall et al. | 623/17.11 |
| 6,520,907 B1 * | 2/2003 | Foley et al. | 600/114 |
| 6,540,747 B1 | 4/2003 | Marino | |
| 6,648,915 B2 | 11/2003 | Sazy | |
| D484,785 S | 1/2004 | Plumer | |
| 6,689,167 B2 * | 2/2004 | Bagby | 623/17.11 |
| 6,796,999 B2 | 9/2004 | Pinchasik | |
| D503,803 S | 4/2005 | Shalaby et al. | |
| 6,921,403 B2 | 7/2005 | Cragg et al. | |
| 6,966,930 B2 * | 11/2005 | Arnin et al. | 623/17.11 |
| D521,858 S | 5/2006 | Roy | |
| 7,060,089 B2 | 6/2006 | Ley et al. | |
| 7,238,205 B2 | 7/2007 | Karahalios | |
| 7,241,313 B2 | 7/2007 | Unwin et al. | |

(Continued)

FOREIGN PATENT DOCUMENTS

WO   WO 2004/043278 A1 *   5/2004

OTHER PUBLICATIONS

Office for Harmonization of the Internal Market (OHIM). Design No. 000069562-0003 (industrial design). Registered Aug. 14, 2003, to NuVasive, Inc.

(Continued)

*Primary Examiner*—Eduardo C. Robert
*Assistant Examiner*—Ellen Rust
(74) *Attorney, Agent, or Firm*—John P. O'Banion

(57) ABSTRACT

A minimally invasive, fluoroscopically guided system is disclosed for stabilizing the articular facet joints of adjacent vertebrae. Ring and dowel implants are disclosed for installation into the facet joint. The invention includes a novel spine surgical training aid used in the initial surgeon training process for refreshing the surgeon's perspective of the critical three dimensional anatomy of the vertebrae. The invention also includes a surgical kit having a range of size-specific drills, inserters, impactors and custom-length long k-wires matched to the internal diameter of the instrumentation system.

25 Claims, 18 Drawing Sheets

U.S. PATENT DOCUMENTS

| | | |
|---|---|---|
| 7,270,675 B2 | 9/2007 | Chun et al. |
| 2002/0026192 A1 | 2/2002 | Schmiel et al. |
| 2002/0055781 A1 | 5/2002 | Sazy |
| 2002/0055782 A1 | 5/2002 | Bagby |
| 2002/0072800 A1 | 6/2002 | Goble et al. |
| 2003/0028251 A1 | 2/2003 | Mathews |
| 2003/0105527 A1 | 6/2003 | Bresnia |
| 2003/0191536 A1 | 10/2003 | Ferree |
| 2004/0068322 A1 | 4/2004 | Ferree |
| 2004/0097927 A1 | 5/2004 | Yeung et al. |
| 2005/0124993 A1* | 6/2005 | Chappuis .................... 606/61 |
| 2005/0240188 A1* | 10/2005 | Chow et al. .................. 606/72 |
| 2006/0064099 A1* | 3/2006 | Pavlov et al. ................. 606/72 |
| 2006/0111782 A1* | 5/2006 | Petersen .................. 623/17.11 |

OTHER PUBLICATIONS

Office for Harmonization of the Internal Market (OHIM). Design No. 000069562-0004 (industrial design). Registered Aug. 14, 2003, to NuVasive, Inc.

Office for Harmonization of the Internal Market (OHIM). Design No. 000730676-0003 (industrial design). Registered May 29, 2007, to LIMA LTO, S.p.A.

Office for Harmonization of the Internal Market (OHIM). Design No. 000730676-0008 (industrial design). Registered May 29, 2007, to LIMO LTO, S.p.A.

Magerl, FP, "Stabilization of the Lower Thoracic and Lumber Spine with External Skeletal Fixation," Clin Orthop Relat Res., Oct. 1984, (abstract) 1 pg.

* cited by examiner

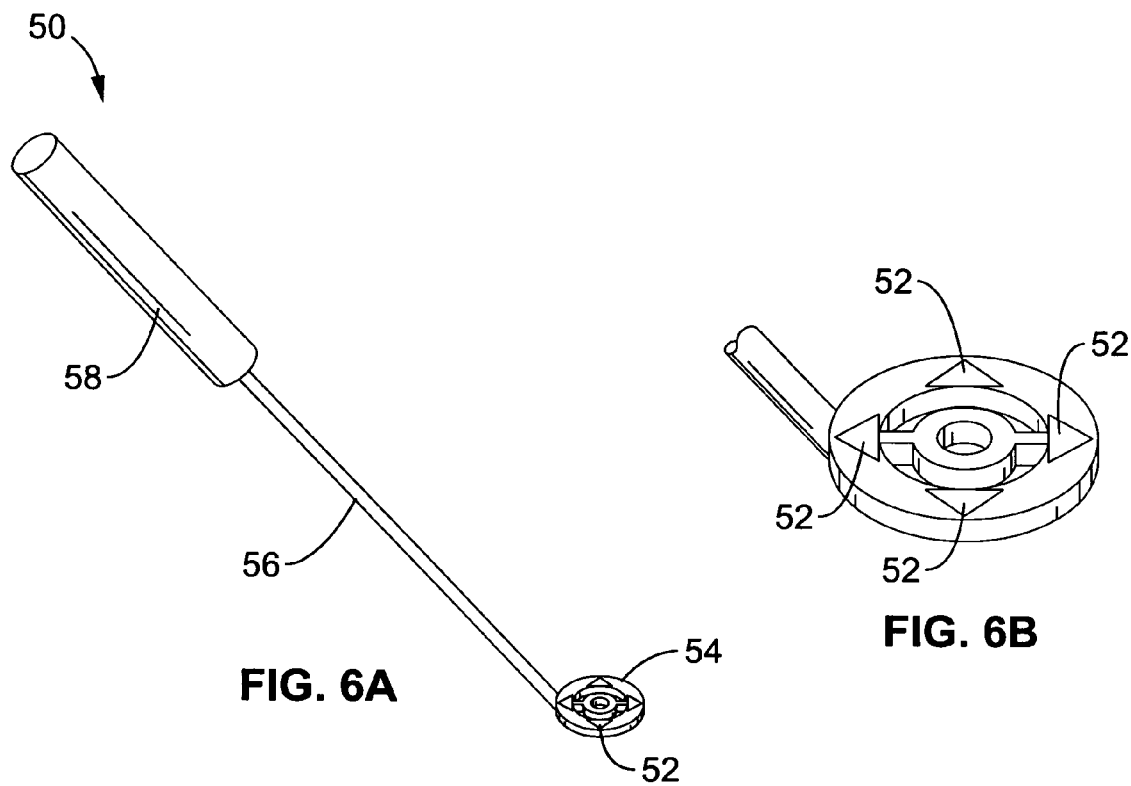
FIG. 6A
FIG. 6B
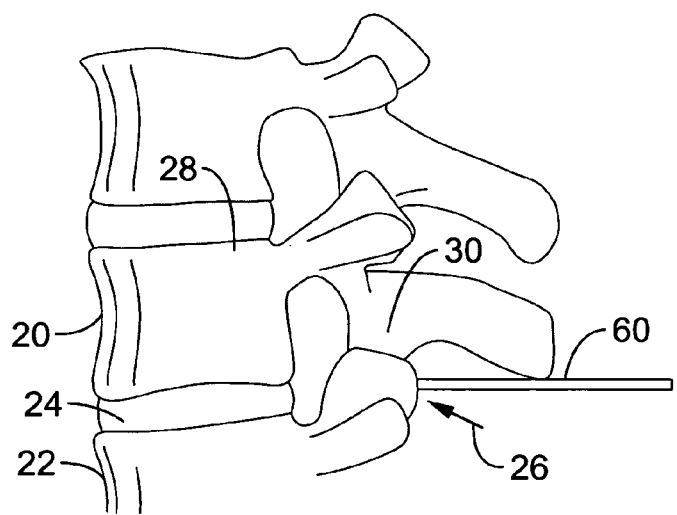
FIG. 7

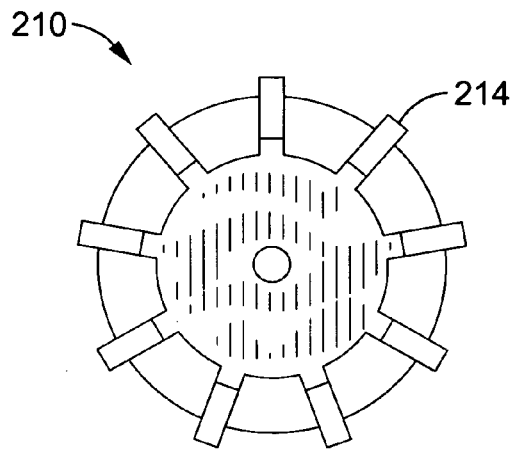
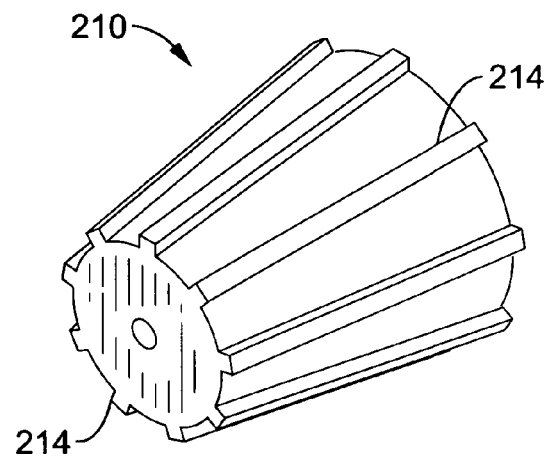
FIG. 16A  FIG. 16B
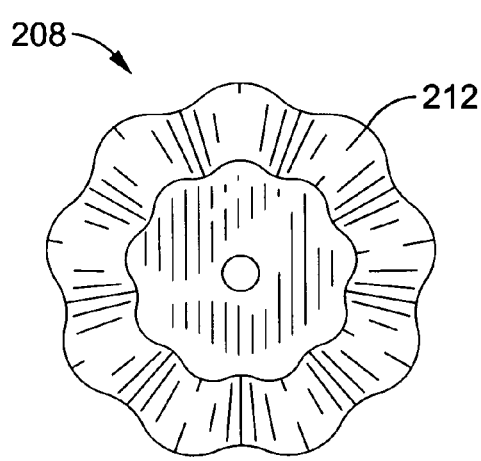
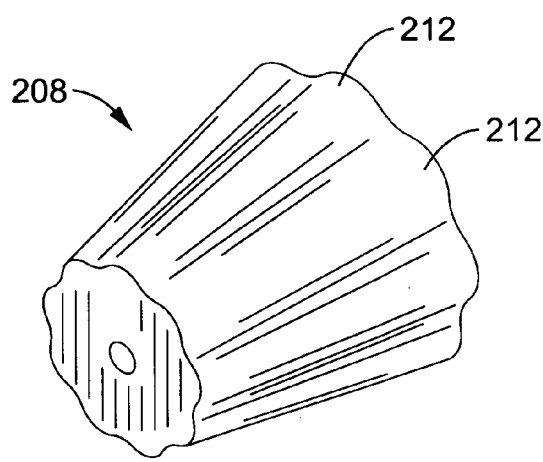
FIG. 16C  FIG. 16D

SPINE MICROSURGERY TECHNIQUES, TRAINING AIDS AND IMPLANTS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to human spinal implant systems and methods, and more particularly to implant systems and methods for stabilizing the facet joints of adjacent vertebrae.

2. Description of Related Art

Chronic back problems cause pain and disability for a large segment of the population. In many cases, the chronic back problems are caused by intervertebral disc degeneration and loss of stability of the intervertebral joint. Over time, the process of aging produces progressive dehydration and loss of height of the intervertebral discs. The shortening of the spinal articular segment produces increased mechanical wear of the facet joints. With the increasing pressure across the facet joints, the articular cartilage on each surface of the joints undergoes abrasive thinning, producing pain. Indications for fusion of the spine include trauma, tumor, infection, and; most commonly, the consequences of degenerative change: progressive deformity, and instability producing compression of the neural elements and intractable pain. In the majority of current spinal fusion cases, successful stabilization of the spinal motion segment is achieved through posterior-lateral lumbar fusion, the biomechanical key to which is successful immobilization of the facet joints.

Currently there exists no direct, efficient procedure to achieve consistent fusion or arthrodesis of the posterior-lateral facet joints of the lumbar spine. The vast majority of spine instrumentation systems bypass the facet joint, spanning the posterior vertebral articulations, immobilizing the facet joint indirectly through transpedicular linkage of adjacent vertebrae. There are multiple clinical indications for the performance of a posterior-lateral lumbar fusion and well over 100,000 are performed each year in the United States alone. The ultimate measure of success of spinal fusion is the elimination of motion of the vertebral motion segment. The ultimate measure of success of posteriolateral spinal fusion surgery depends upon solid fusion of the facet joints at each level. For many years the success rate for lumbar fusion surgery has remained unchanged at approximately 85%. The ideal procedure would achieve a 100% predictable spinal fusion using a safe, minimally invasive method to mechanically lock the motion segment in order to allow bone formation and fusion across the facet joints with minimal tissue disruption.

The classic procedures for posterior-lateral fusion of the lumbar spine require long posterior midline incisions, are frequently associated with massive blood loss occurring during prolonged operations, produce widespread paraspinous muscle damage resulting from the extensive retraction forces necessary for visualization, and yield unacceptably high clinical failure rates. The cost of failed spine surgery is enormous. Persistent pain, lost productivity and the disappointingly low success rate of revision surgery underscore the need for more effective primary lumbar spine fusion surgery.

Spinal fusion techniques have evolved significantly since the first successful fusions were reported by Hibbs (Hibbs R A: An operation for progressive spinal deformities. N Y Med J 93:1013-1016) and Albee in 1911 (Albee F H: Transplantation of a portion of the tibia into the spine for Pott's disease. JAMA 57:885-886.) The importance of the facet joint in the success of posterior spine fusion surgery was stressed by McBride in 1948 (McBride E D: A mortised transfacet bone block for lumbosacral fusion. J Bone Joint Surg [AM] 31:385-393.). McBride described a fusion technique to eliminate intervertebral motion at the facet articulation by excavating a rectangular cavity, or mortise, and impacting a dovetailed graft into this area while using intraspinous distraction to assist with graft placement.

The first descriptions of the use of metallic trans-articular implants to obtain internal fixation of the spine as an adjunct to lumbar fusion was reported in the 1940's by Toumey (Toumey J W (1943): Internal fixation in fusion of the lumbosacral joints. Lahey Clin Bull 3:188-191.) and King (King D (1944): Internal fixation for lumbosacral fusion. Am J Surg 66:357-361). These techniques for stabilization of a lumbosacral fusion relied on passing a short bone screw from medial to lateral across the facet joints of the level to be fused bilaterally. Unacceptably high non-union rates associated with these techniques led investigators to develop other methods of spinal instrumentation which spanned or did not rely solely on fixation of the facet joints.

Interest in the facet joint as a key to successful posterior fusion was renewed by Magerl who introduced another variation of facet fixation in which a long slender bone screw was placed from the base of the spinous process on one side, between the two tables of the lamina on the opposite side and then across the facet joint into the base of the transverse process (Magerl F P (1984): Stabilization of the lower thoracic and lumbar spine with external skeletal fixation. Clin Orthop 189:125). Magerl's technique improved the success rate of posterior spine fusions through the use of a long implant fixed to the bone at multiple points which solved the major problem of loosening due to failure of the bone-implant interface. Translaminar facet screw fixation has not been widely adopted since it is much more technically demanding than other current fixation systems, requires multiple incisions, places the dura at risk and depends upon an intact lamina.

Current advances in spine surgical techniques involve the development of minimally invasive, tissue sparing approaches performed through tiny incisions under television image intensifier fluoroscopic guidance.

For these reasons, it would be desirable to provide a new system to provide definitive fixation of the facet joints of the lumbar spine applied through a minimally invasive approach under fluoroscopic guidance.

It would further be desirable to provide a vertebral anatomy training device for demonstrating the precision fluoroscopic beam positioning critical for minimally invasive spine surgery.

It would further be desirable to provide a training aid useful in the initial and follow-up training to aid physicians and their surgical teams in visualizing important aspects of image guided spine surgery procedures.

At least some of these objectives will be met with the invention described herein.

BRIEF SUMMARY OF THE INVENTION

The system and methods of the present invention provide a comprehensive, minimally invasive surgical solution to the biomechanical problems currently encountered by spine surgeons. The system includes a novel spine surgical training aid used in surgeon education, for ongoing use as a pre-operative reference to the critical three dimensional anatomy of the vertebrae, and as a simple method of teaching the fluoroscopy technician how to provide perfect reproducible views of each vertebrae during the procedure. The training aid has broad utility in enhancing the safety of all of the current minimally invasive spine surgical procedures.

The system of the present invention also includes novel planning and placement technology, which allows the surgeon to percutaneously place a sizing guide on the spine to fluoroscopically assess the appropriate implant size. The fluoroscopic "facet joint view" and other radiographic landmarks described in the FacetLock™ procedure guide are unique to this system. The system also includes series of clear acetate radiographic overlay templates of different scales printed with outlines of the implants for use during the surgeon's pre-operative planning process.

The invention also includes a surgical kit having a range of size-specific drills, inserters, impactors and custom-length guide wires matched to the internal diameter of the instrumentation system.

An aspect of the invention is a method for stabilizing adjacent vertebrae of the spine, the adjacent vertebrae comprising superior and inferior articular processes forming first and second bilateral posterior facet joints each having opposing subchondral articular surfaces. The method generally comprises forming a path into the subchondral bone of the articular surfaces of the first facet joint, and installing an implant into the bone path of the first facet joint, wherein the implant is configured to immobilize the first facet joint of the articulation between the two adjacent vertebrae.

The method may further comprise forming a path into the subchondral bone of the articular surfaces of the second facet joint, and installing an implant into the scored bone path of the second facet joint to immobilize the second facet joint.

In a preferred embodiment, forming the bone path is achieved by drilling a cylindrical bore into the subchondral articular surfaces, wherein a portion of each subchondral articular surface is removed to form grooves defining opposite ends of the cylindrical bore. More preferably, the cylindrical bore is drilled in a path substantially parallel to the planes of the subchondral surfaces.

Generally, the method is performed percutaneously, i.e. through a small skin incision, with image intensified fluoroscopic guidance in which the critical anatomy of the adjacent vertebrae is visualized on the screen of a monitor. For example, size of the implant may be determined by positioning a radiolucent implant guide over the bone of the facet joint and comparing the size on the image seen on the monitor.

In a preferred embodiment, the bone path is formed by fluoroscopically visualizing the planes of the subchondral surfaces of the facet joint, determining the size of the bone path, installing a blunt dilator through the soft tissues of the paraspinous musculature, down to the outer surface of the facet joint; and drilling a cylindrical bore into the opposing articular processes, wherein the blunt dilator guides the path of the cylindrical bore. The drill may comprise a hollow core drill with an inside diameter matching that of the dilator such that the drill may be advanced over the dilator to score kerfs into the opposing articular processes.

In a preferred method of the present invention, a guide wire is installed into the facet joint to aid in positioning the instruments and implant to the implant site. For example, the blunt dilator may be positioned at the facet joint by advancing it over the guide wire. The dilator is optimally configured to limit the depth of the bored bone path. Typically, the bone path is drilled to a depth of approximately 75% of the facet joint bone mass. A radiolucent implant guide is positioned at the facet joint to measure the size of the bone path.

In one embodiment of the invention, an oversized dowel is driven into the scored bone path to create an interference fit with opposing first and second vertebrae to mechanically lock the articulation of the first facet joint.

Alternatively, a ring implant is driven into the cylindrical kerfs formed in the articular processes, the ring implant constraining motion of the facet joint through circumferential tension band effect.

In another aspect of the invention, an implant is disclosed for stabilizing two adjacent vertebrae of the spine, the adjacent vertebrae forming first and second facet joints each having opposing subchondral articular surfaces. The implant generally comprises a dowel configured to be installed into a bone path, the bone path bored into the opposing subchondral surfaces, wherein the dowel has an outer surface configured to create an interference fit within and between the posteriolateral articulations of the first and second vertebrae. In such a configuration, the implant provides a mechanical lock of the facet joint articular surfaces to resist the shear forces produced by the physiologic bending of the vertebral articulation.

In one embodiment, the outer surface of the dowel has an outer diameter sized to create the interference fit with the bilateral opposing facet articular processes of the adjacent vertebrae. The outer surface may preferentially be tapered to create the interference fit between the implant and the osseous structure of the opposing facet joint articular processes, the taper emanating from a leading edge of the dowel.

In addition, the outer surface may be roughened to create the interference fit the first and second vertebrae. For example, the roughened external surface may comprise tantalum beads or other materials which are biocompatible with ingrowth of bone into the outer surfaces of the implant. The roughened external surface may also be plasma sprayed with calcium hydroxyapatite crystals to enhance the immediate biologic fixation of the implant with the surrounding cancellous bone. In addition, the roughened external surface may have undulations, teeth or ridges. Ideally, the external surface of the implant is configured to interdigitate with the bone surrounding the joint surfaces providing an immediate mechanical interlock of the intervertebral facet articulations. Immediate mechanical immobilization of the highly cellular periarticular cancellous bone exposed by the drilling and implantation of the device is an important aspect of the implant system, which is beneficial in protecting the cellular healing response which produces the bone formation and osseous fusion through the implant and between the articular processes of the adjacent vertebrae to promote osseous fusion.

The dowel is preferably cannulated along its insertional axis for installation into the facet joint via a guide wire. The outside diameter of the dowel ranges from 6 mm to 12 mm, and the dowel ranges from 4 mm to 12 mm in length.

In yet another aspect of the invention, an implant is disclosed for stabilizing first and second adjacent vertebrae of the spine, the adjacent vertebrae comprising articular processes forming bilateral first and second facet joints each having opposing subchondral articular surfaces. The implant generally comprises a ring configured to be installed into a cylindrical kerf bone path bored into the opposing articular processes. The ring has an outer surface configured to create an interference fit with the surrounding bone of the kerf such that the ring constrains facet joint motion through circumferential tension band effect when installed. The ring configuration, its strength of fixation depending upon a tension band restraint of facet joint motion, may be fabricated from titanium or similar metal, or a bioabsorbable material such as carbon fiber or a bioabsorbable polymer.

In some embodiments, the outer surface has an outer diameter sized to create the interference fit with the bone surrounding the kerf. The outer surface may also be roughened to create the interference fit. The roughened external surface may have one or more fenestrations, the fenestrations promoting growth of cancellous bone surrounding the ring. The fenestration may comprise circular holes or parallel columns running axially along the outer cylindrical surface. The fenestrations may also have raised edges at their perimeters, the raised edges forming an interference fit with the surrounding bone of the kerf. In addition, the outer surface may also have a tapered leading edge to facilitate installation of the ring.

In another aspect of the invention, a kit for preparing an implant site for percutaneously installing an implant between adjacent first and second vertebrae of a patient comprises a guide wire having a length configured to span to the implant site from a location exterior to the patient, a cannulated dilator configured to be received on the guide wire such that the dilator can be positioned at the implant site by advancing it along the guide wire, and a drill configured to bore a bone path at the implant site. The drill has a hollow core with an internal diameter closely matching the outer diameter of the dilator such that the drill can be positioned at the implant site by advancing it over the dilator.

In a preferred embodiment, the dilator is configured to be positioned at the facet joint formed by the first and second vertebrae, and wherein the drill has an outer diameter configured to bore a kerf into opposing articular processes of the facet joint. The drill will typically have an outer diameter ranging from 6 mm to 12 mm. Ideally, the dilator has a stop to limit the depth of the drill.

The kit may also include a cannulated impactor configured to be received on the guide wire such that the impactor may be positioned at the implant site by advancing it along the guide wire to drive the implant into the bone path.

In a further aspect of the invention, a system is disclosed for percutaneously installing an implant at an implant site to stabilize two adjacent first and second vertebrae of a patient. The system generally has a guide wire having a length configured to span to the implant site from a location exterior to the patient, wherein the guide wire assists in positioning the tools and implant necessary to perform the installation. The system also has a cannulated dilator configured to be received on the guide wire such that the dilator can be positioned at the implant site by advancing it along the guide wire, wherein the dilator has an outer diameter correlating to a physiological relationship between the first and second vertebrae. The system further comprises a drill configured to bore a bone path at the implant site, the drill having a hollow core with an internal diameter closely matching the outer diameter of the dilator such that the drill can be positioned at the implant site by advancing it over the dilator. Finally, the system includes an implant sized to be received into the bone path to constrain motion of the first and second adjacent vertebrae, the implant configured to be advanced to the implant site via the guide wire.

In a preferred embodiment, the dilator is configured to be received at a facet joint formed by the first and second vertebrae, and wherein the drill has an outer diameter configured to bore a kerf into opposing articular surfaces processes of the facet joint. A cannulated impactor may also be used to drive the implant into the bone path. In addition, the system may include a radiolucent implant guide which can be positioned at the implant site to determine the size of the implant. The system may further include a radiographic overlay template configured to be placed over radiographic images of the patient to determine the size of the dilator during the surgeon's preoperative planning.

In another aspect of the invention, a training apparatus is disclosed for demonstrating an aspect of an image-guided spine surgery procedure. The training apparatus generally comprises a support, a simulated three-dimensional spine structure disposed on the support, the spine structure comprising a plurality of adjacent vertebrae, and means for demonstrating an aspect of surgical procedure on the simulated spine structure. The superior vertebra or several vertebrae may be removed to be taken to the O.R. by the surgeon for use in pre-operative teaching of the essential fluoroscopic landmarks to the remainder of the surgical team.

In a preferred embodiment, the training device includes one or more of color coded regions correlating to an area of interest for a step in the procedure. Each simulated vertebrae is bored out along the locus of safe passages from the point of initial approach on the posterior-lateral portion of the vertebra which will be blindly transgressed during a fluoroscopically-guided cannulation of the pedicle in an approach to the center of the vertebral body. This 'hollowing out' of the safe instrument trajectory fields within the vertebrae provides a clear visualization of the anatomy which the surgeon and his/her fluoroscopic technician will see on the image monitor during the actual surgical procedure. The training apparatus may also comprise one or more color coded glass markers, such as erasable marking crayons, for reference to anatomical images on a radiographic display, the colors of the markers correlating to the colors of the coded regions of the spine structure. The color-coded, clear step-wise approach to the positioning of the fluoroscope, combined with the clear image of the geometry of the training aid creates a reproducible, safe approach to the complex spinal anatomy, surrounded on all sides by delicate structures.

In another aspect of the invention, the highlighted three dimensional vertebral anatomy and distinctive color coded regions of the training aid are reproduced in a three dimensional graphic computer program which is used during initial surgeon training and as a refresher for pre-operative review of the technique and relevant fluoroscopic anatomy. The program, which allows three axis manipulation of the fluoroscopic perspective of the vertebral anatomy, may be given to surgeons completing training, and may be accessible through the internet from a central server and may be used in patient educational and promotional materials.

A method for simulating a minimally invasive, fluoroscopically guided spine surgery may comprise generating a three-dimensional simulation of a human spine having plurality of adjacent vertebrae via a computer; generating a plurality of color coded regions for demonstrating an aspect of surgical procedure on the simulated spine structure; and outputting said three-dimensional simulated spine structure and color coded regions to a display. The displayed simulated spine structure may be rotated to view a particular orientation of the vertebrae and steps necessary to perform an image guided surgical procedure.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 6A-B illustrate a radiolucent implant guide in accordance with the present invention.

FIG. 7 illustrates a lateral view of the lumbar spine with a guide wire installed in the facet joint.

Figure 8:
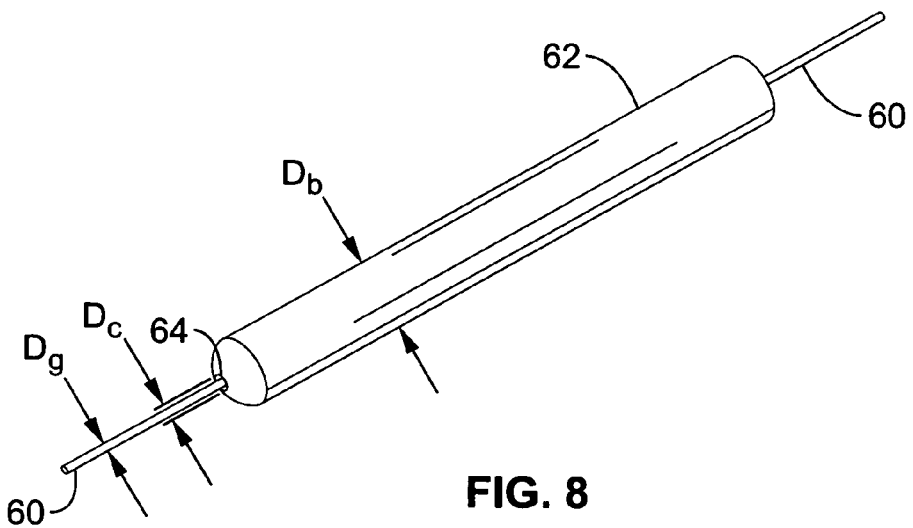

FIG. 8 illustrates a dilator advanced along the guide wire of FIG. 7 in accordance with the present invention.

Figure 9A:
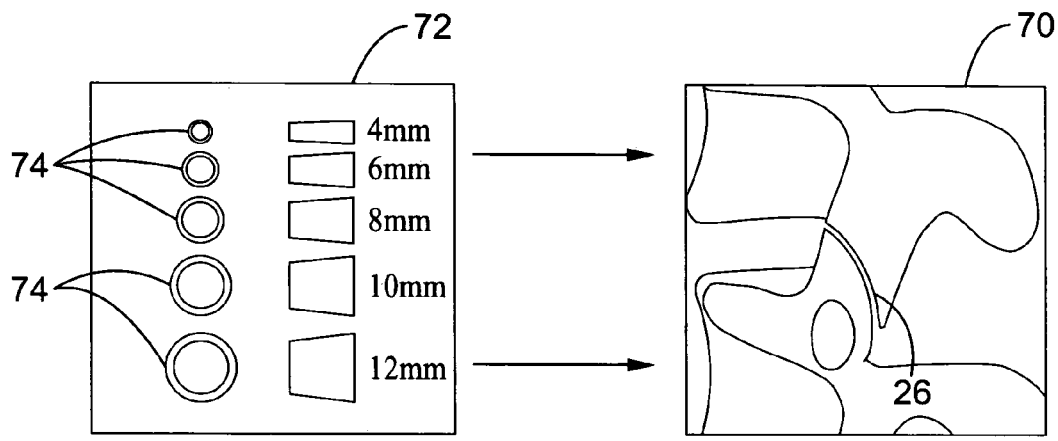
Figure 9B:
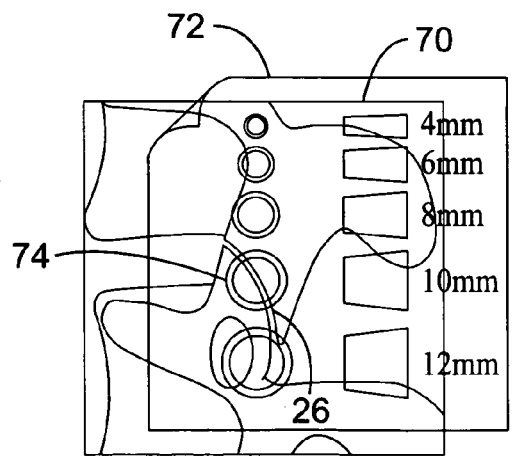

FIGS. 9A-B illustrate an overlay template and radiographic image in accordance with the present invention.

Figure 10A:
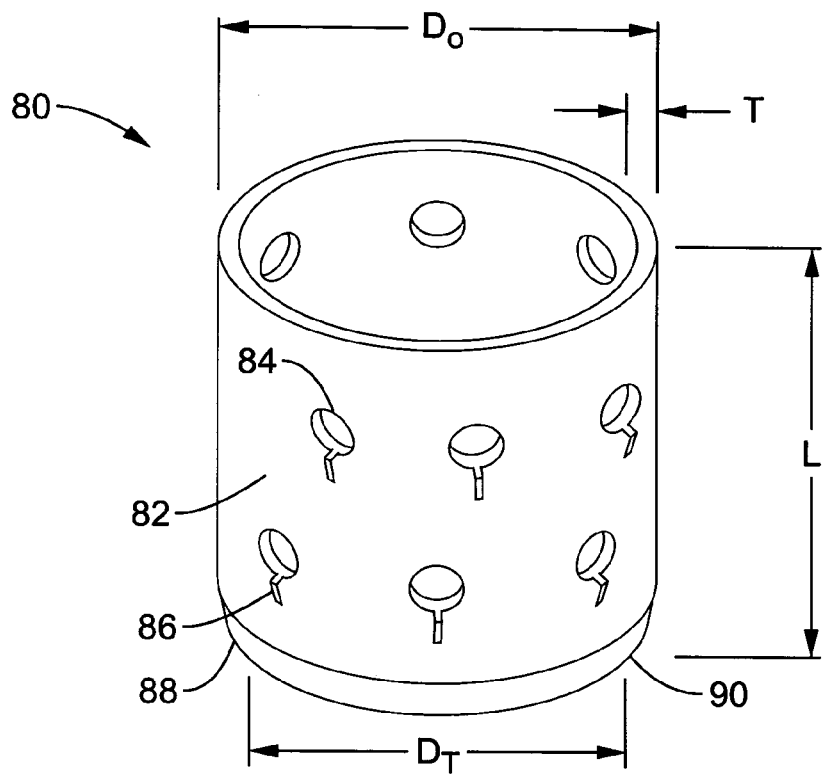
Figure 10B:
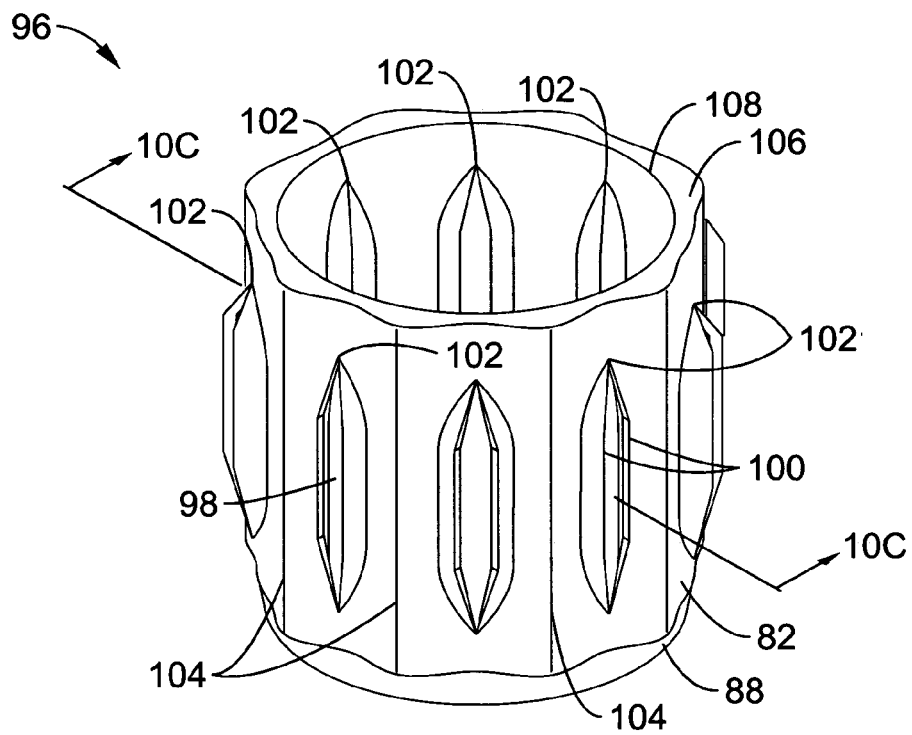

FIGS. 10A-B illustrate exemplary ring implants in accordance with the present invention.

Figure 10C:
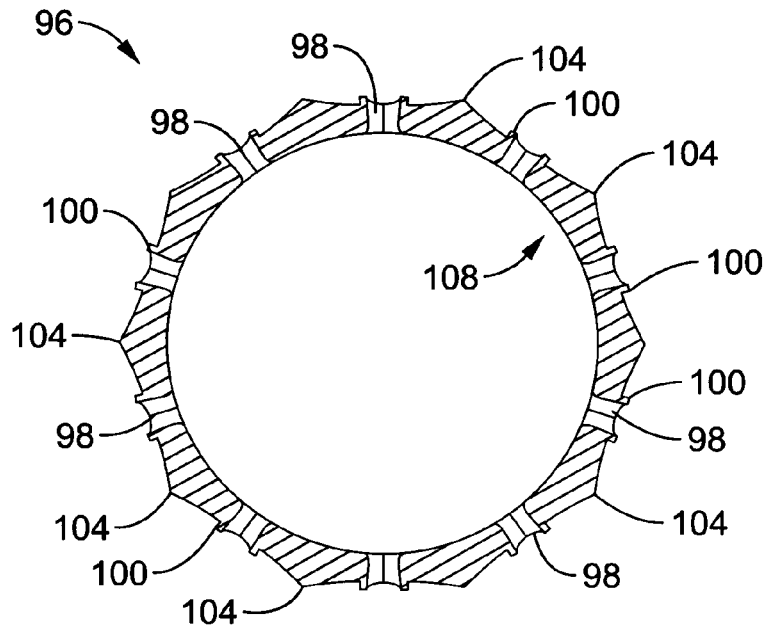

FIG. 10C illustrates a cross-section view of the ring implant of FIG. 10B.

Figure 10D:
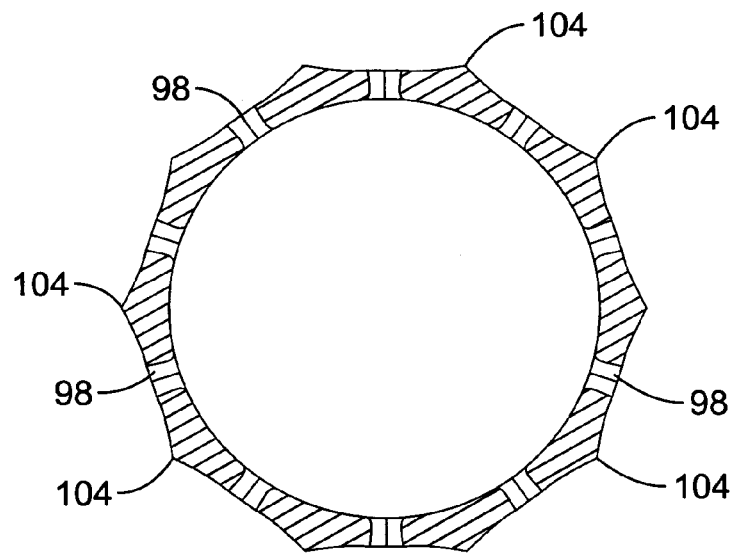

FIG. 10D illustrates an alternative cross-section view of the ring implant of FIG. 10B.

Figure 11:
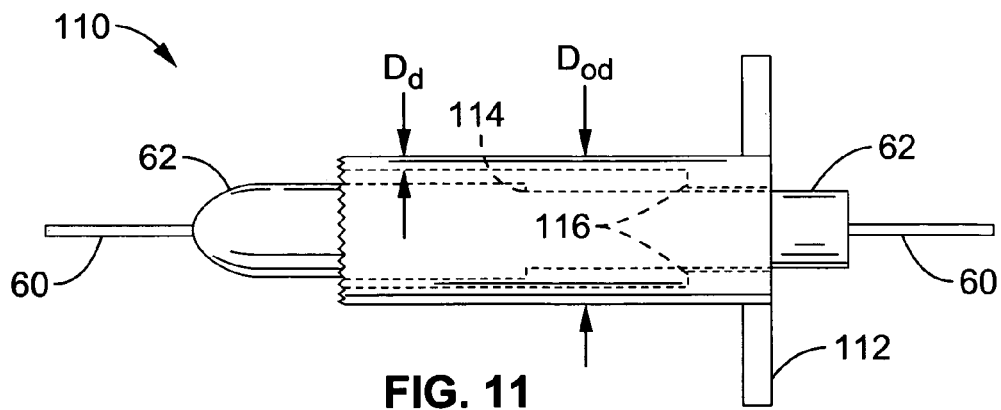

FIG. 11 illustrates a hollow core drill advanced along the guide wire of and dilator of FIG. 8 in accordance with the present invention.

Figure 12:
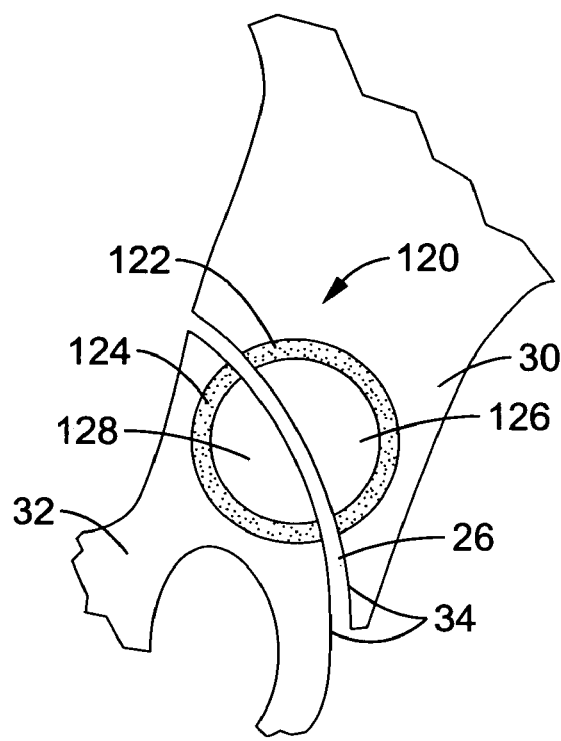

FIG. 12 illustrates a tubular bone path or "kerf" scored into the articular processes in accordance with the present invention.

Figure 13:
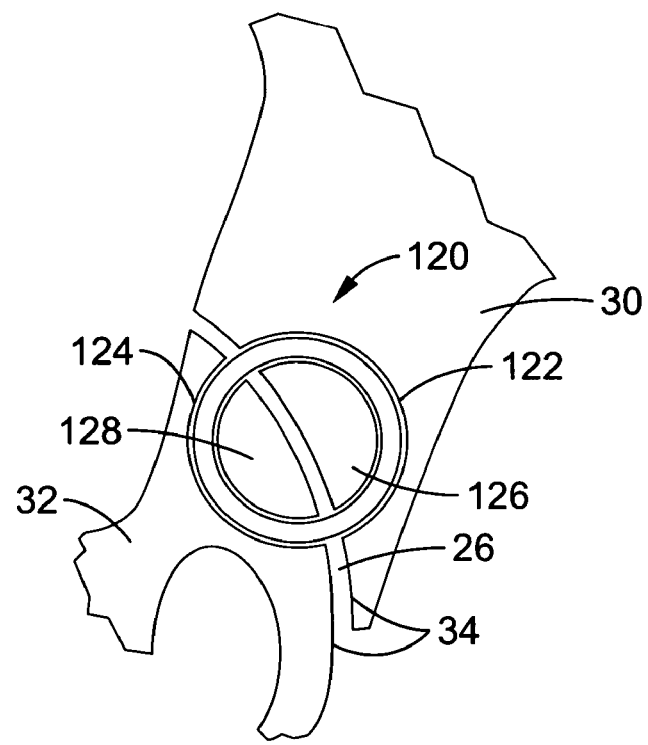

FIG. 13 shows a ring implant installed in the bone path of FIG. 12.

Figure 14:
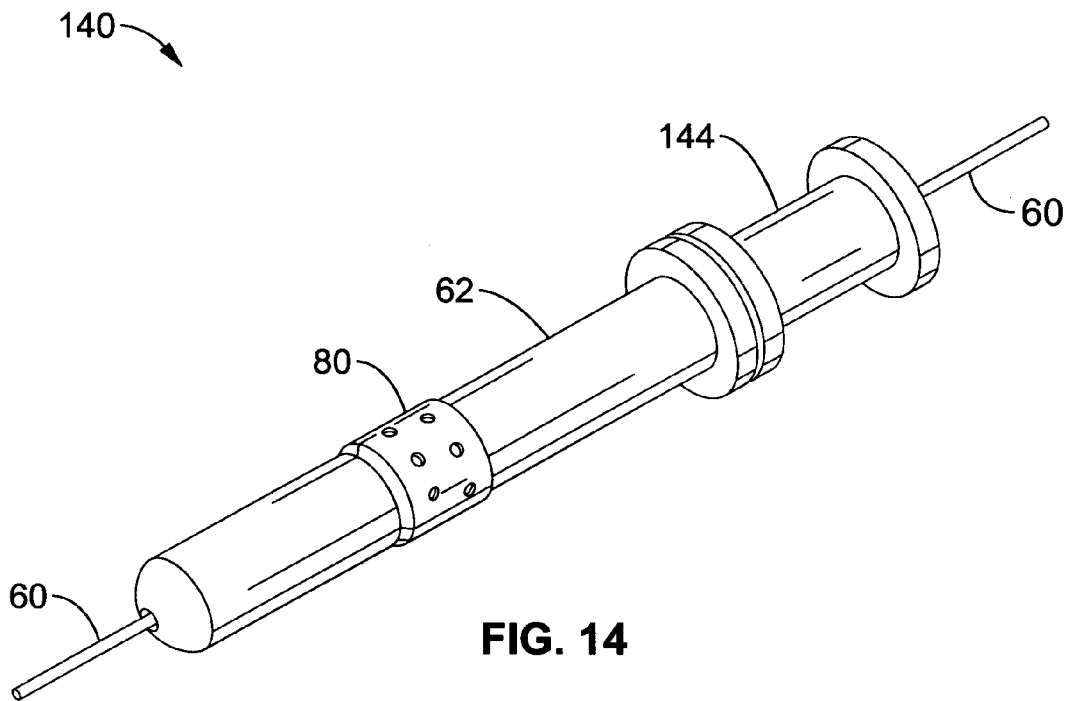

FIG. 14 illustrates an impactor advanced along the guide wire and dilator of FIG. 8 in accordance with the present invention.

Figure 15:
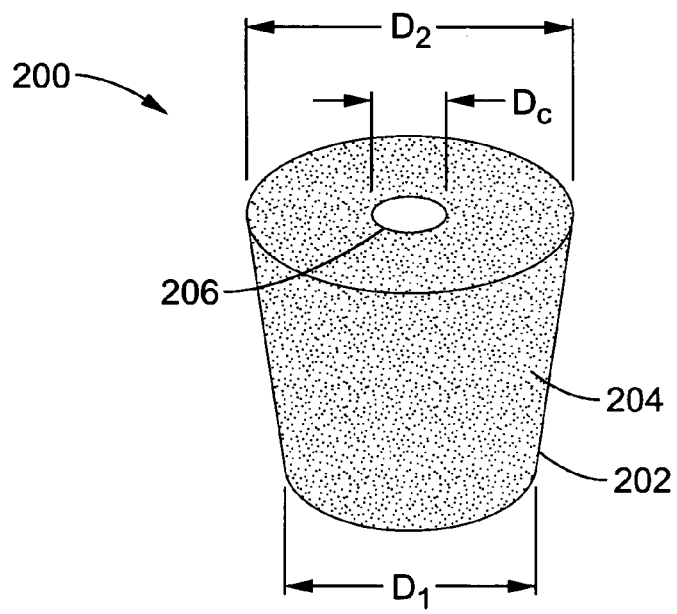

FIG. 15 illustrates exemplary dowel implant in accordance with the present invention.

FIGS. 16A-D illustrate dowel implants with alternative outer surfaces.

Figure 17:
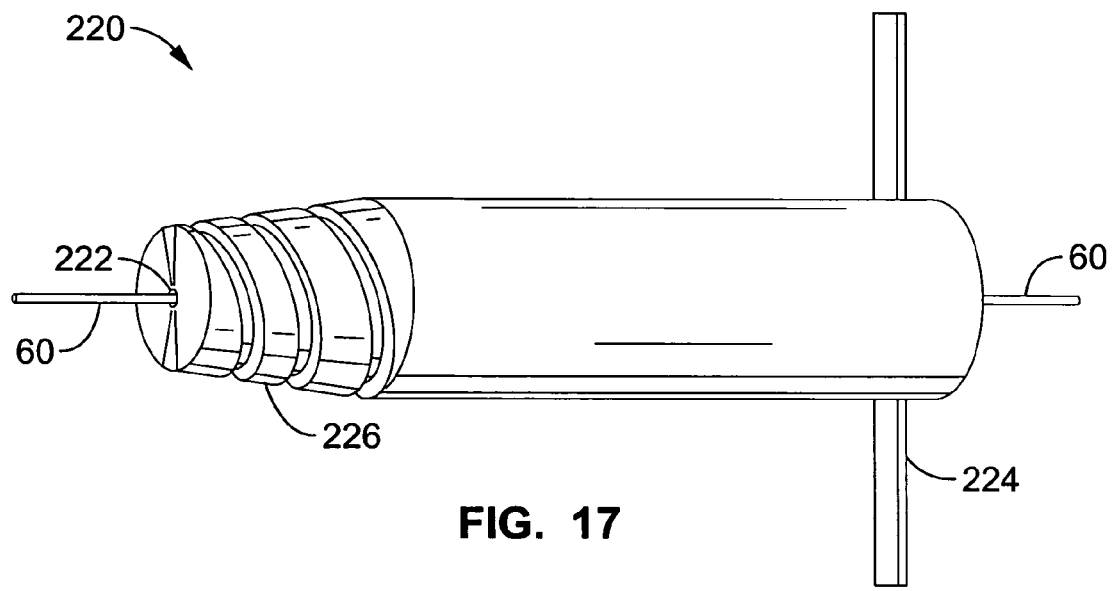

FIG. 17 shows a tapered drill advanced along a guide wire in accordance with the present invention.

Figure 18:
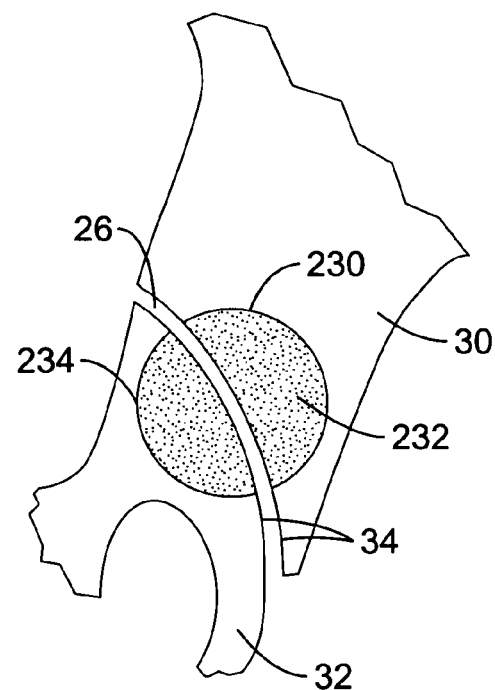

FIG. 18 illustrates a dowel implant bone path scored into the articular processes.

Figure 19:
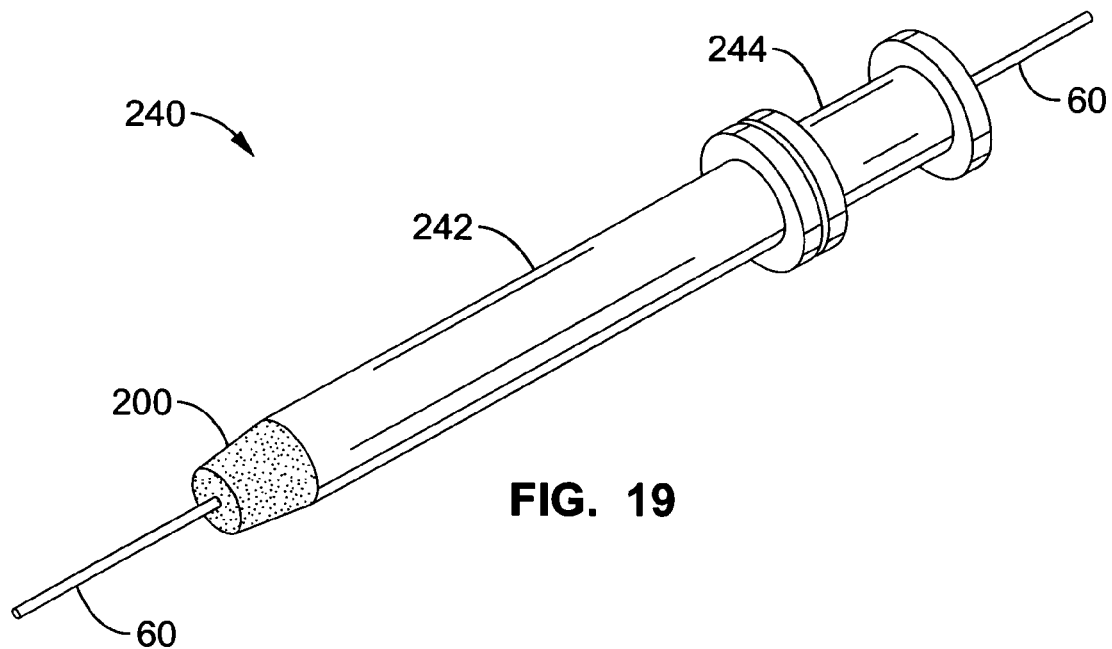

FIG. 19 illustrates an impactor and dowel implant advanced along a guide wire and dilator in accordance with the present invention.

Figure 20:
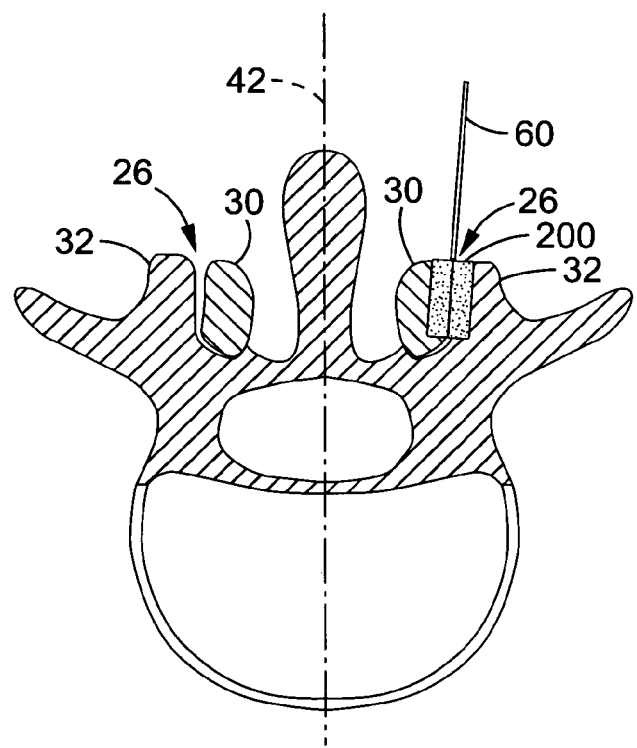

FIG. 20 illustrates a top sectional view of an installed dowel implant.

Figure 21:
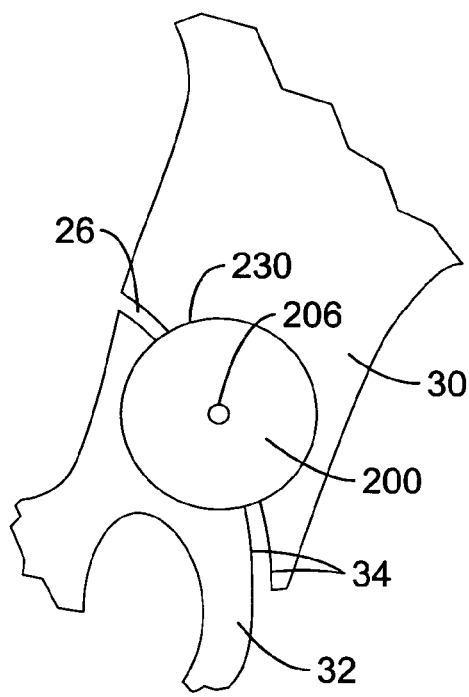

FIG. 21 illustrates a posterior-lateral view of an installed dowel implant.

Figure 22:
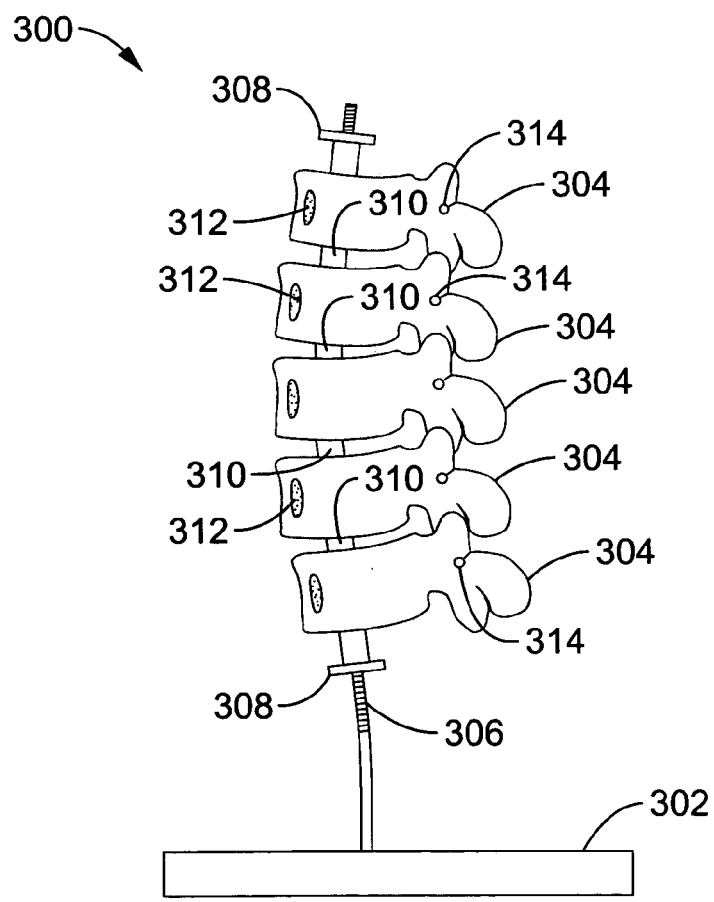

FIG. 22 shows a schematic view of a training device in accordance with the present invention.

Figure 23:
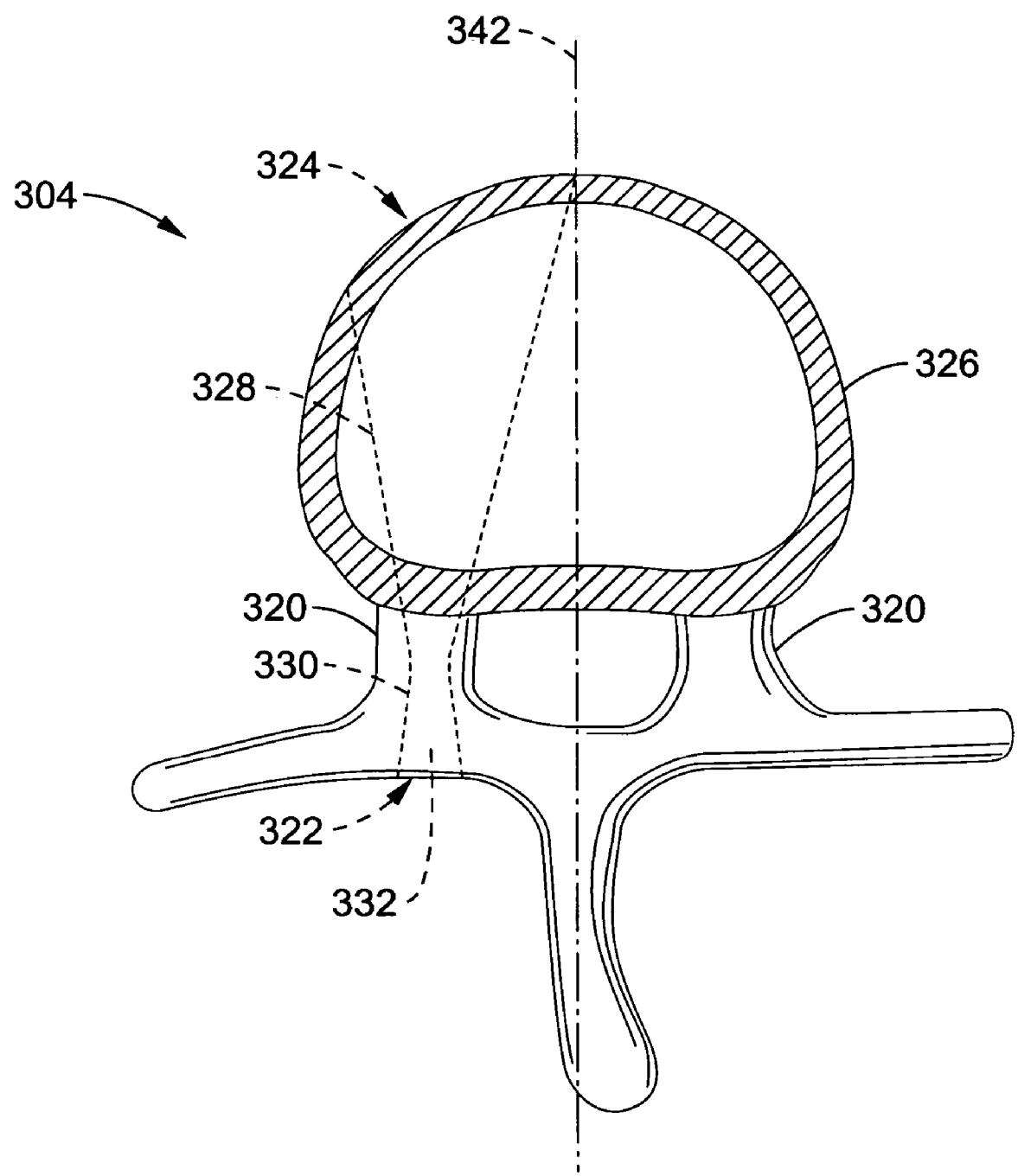
Figure 24:
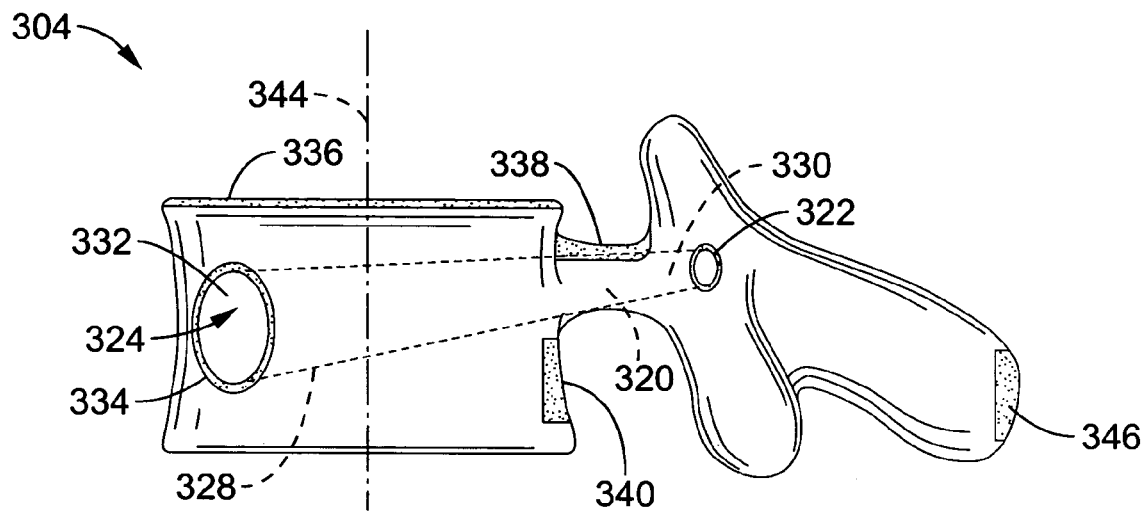

FIG. 23 is a top view of a horizontal section of an individual vertebral segment model of the training aid taken just above the junction of the pedicles with the vertebral body FIG. 24 is a left side view of the lateral aspect of a segment of the vertebral anatomy and fluoroscopic positioning training aid showing the color-coded surface regions and a schematic representation of the internal boring.

Figure 25:
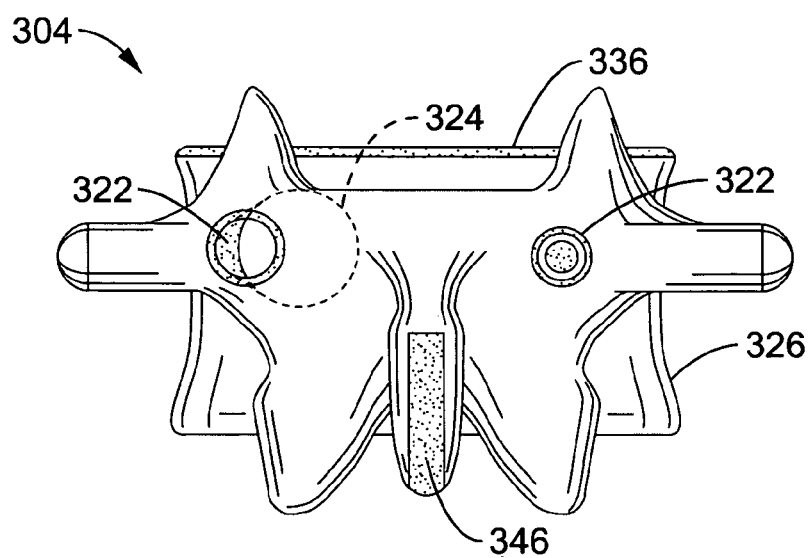

FIG. 25 is a posterior view of a segment of the training aid showing the color-coded regions, surface modification illustrating the starting point for pedicle cannulation and schematic representation of the internal boring.

Figure 26:
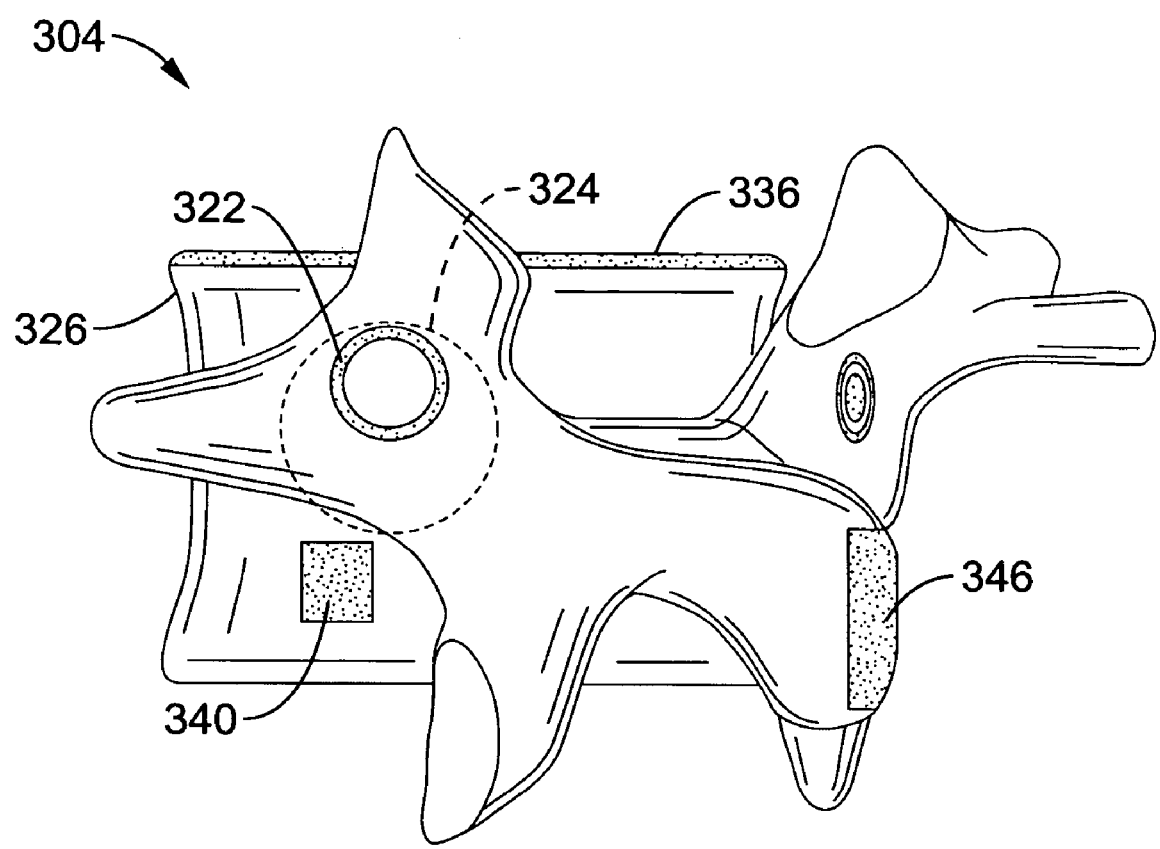

FIG. 26 is an oblique view of the posterior-lateral aspect of the vertebral segment in which the viewer's eye is precisely lined up with the axis of the central pathway through the pedicle into the vertebral body.

FIGS. 27A-D illustrate the color coded landmarks with reference to a representative image that would show up on a fluoroscopic monitor demonstrate the effects of slight rotational mal-positioning about the longitudinal and vertical axes of the vertebral model showing loss of alignment of the highlighted anatomic areas on the model which correspond to similar details on the fluoroscopic image which will be seen intraoperatively. FIG. 24C demonstrates alignment of the reference points on the training aid necessary to produce a perfect lateral fluoroscopic image of the vertebral body.

DETAILED DESCRIPTION OF THE INVENTION

Referring more specifically to the drawings, for illustrative purposes the present invention is embodied in the systems and methods generally shown in FIG. 1 through FIG. 27D. It will be appreciated that the systems may vary as to configuration and as to details of the parts, and that the method may vary as to the specific steps and sequence, without departing from the basic concepts as disclosed herein.

Figure 1:
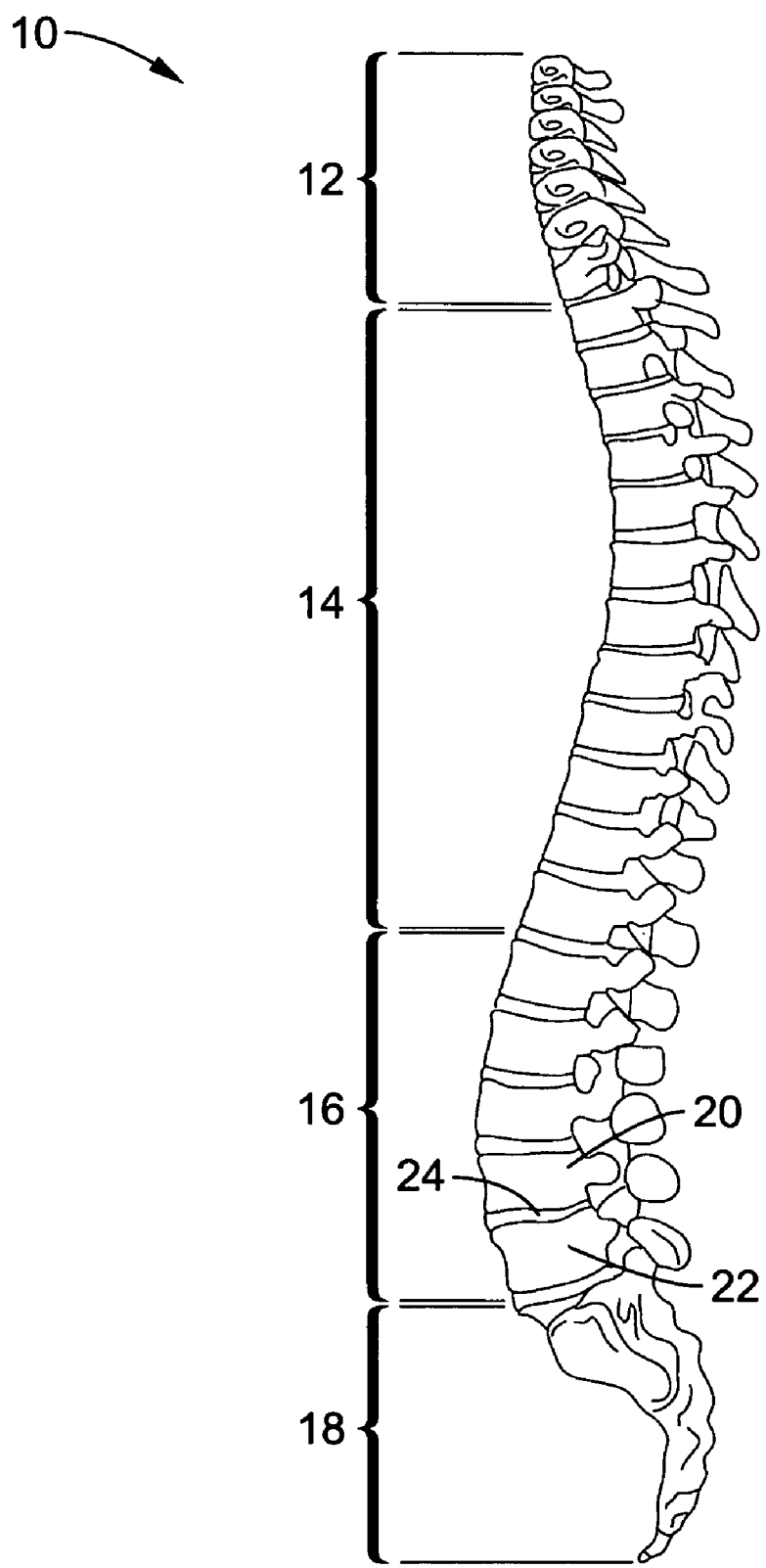
FIG. 1 is a lateral view of the human spine.

Referring to FIG. 1, a lateral view of the human spine 10 is illustrated showing the various regions of vertebrae: cervical 12, thoracic 14, and lumbar 16. The basic biomechanical unit of the spine, referred to as a motion segment, consists of two adjacent vertebrae 20, 22 and the three joint articular complex through which they move and are constrained in relation to one another.

Figure 2:
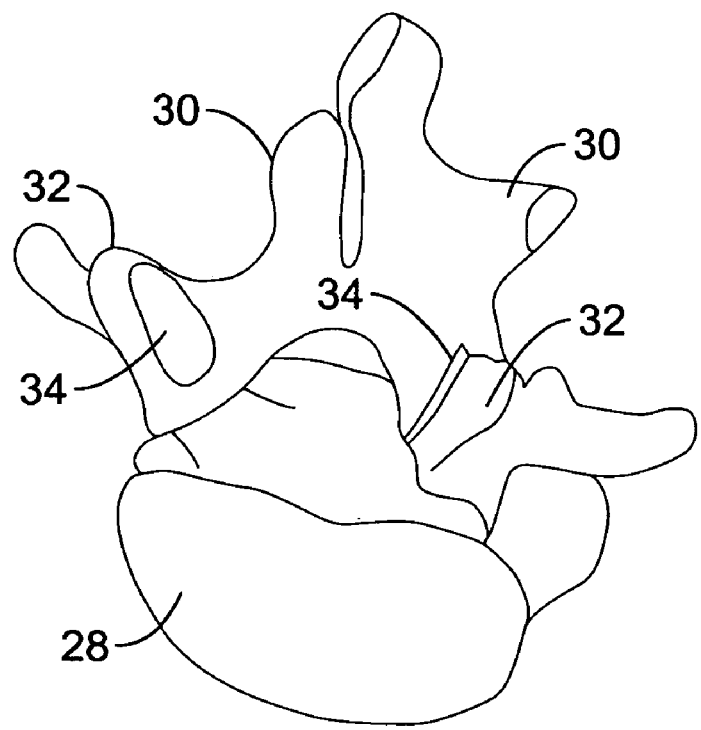
FIG. 2 is an upper-posterior view of a human lumber vertebra.
Figure 3:
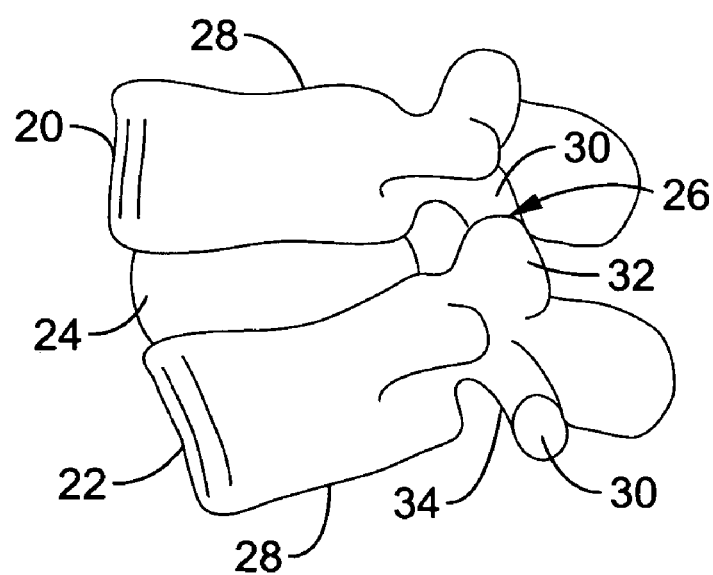
FIG. 3 is a lateral view of two adjacent lumbar vertebrae.

Referring to FIGS. 2 and 3, the lumbar spine articulations consist of an intervertebral disc 24 located between the bodies 28 of the adjacent vertebrae 20, 22, and two facet joints 26 symmetrically located laterally from the sagittal plane at the posterior end of the vertebral body 28. Each facet joint 26 is formed by the opposing subchondral surfaces 34 of the inferior articular process 30 and the superior articular process 32 of adjacent vertebrae.

The facet joints 26 allow constrained spinal motion while protecting the contained neural structures. In general terms the intervertebral disc 24 is a viscoelastic universal joint while the bilateral posterior-lateral facet joints 26 are highly constrained sliding planar articulations, lubricated by synovial fluid contained within a joint capsule. The facet joints 26 bear approximately 20% of the axial force transmitted through the spinal motion segment. There are major differences in the translational and rotational forces imposed on the facet joints in the cervical 12, thoracic 14 and lumbar 16 spines. In the lumbar spine, the geometry of the lumbar facet joints provides a high degree of resistance to translational shear forces across the horizontal transverse plane of the vertebrae, strong resistance to rotation about the longitudinal (sagittal) axis of the spine, while controlling forward and back bending flexion-extension excursion in the frontal plane and lateral bending rotational motion to within physiologic limits. Ultimately, the stability of the spine 10 is defined in terms of its ability to protect the enclosed neural elements.

FIGS. 4-21 illustrate systems methods in accordance with the present invention for performing a minimally invasive procedure to stabilize the facet joints 26 between two or more adjacent vertebrae. One of the major advantages of minimally invasive surgery is the ability to perform the procedure with minimal tissue trauma. Television image intensifier fluoroscopy provides the guidance necessary to allow a surgeon to place instrumentation and implants precisely on the desired anatomic 'target'. A major point of emphasis of the Facet-Lock™ system of the present invention is the concept of absolutely minimizing the impact of the surgery upon the patient's physiology through planned pre-emptive analgesia and minimal tissue trauma. The patient is premedicated pre-operatively with medications blocking the major pathways of transmission of pain from the surgical site. Prior to making the incision, the surgeon should infiltrate the area of the proposed incision with a long-acting local anesthetic. At each step, the FacetLock™ procedure guide provides guidance and techniques to provide local anesthesia during the procedure.

Figure 4:
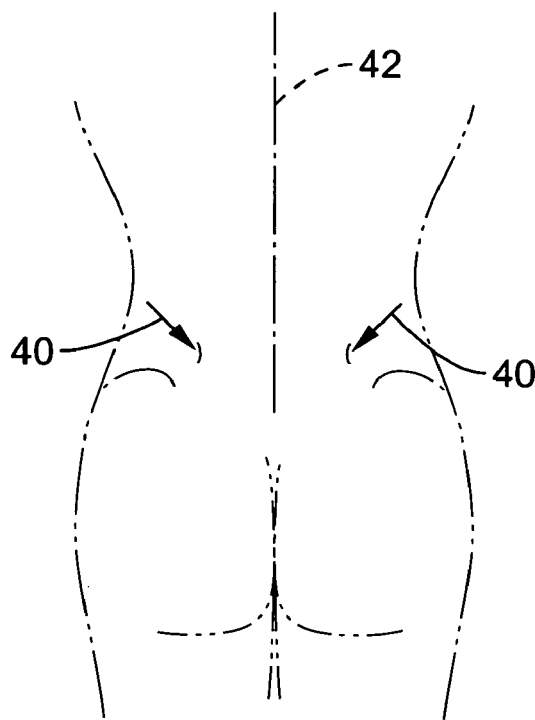
FIG. 4 is a posterior view of a patient in preparation for spinal surgery.

Referring to FIG. 4, at the beginning of the surgical procedure bilateral posterior skin markings 40 are drawn on the patient's skin at generally. symmetric locations lateral from the midline 42 using fluoroscopic guidance by locating landmarks 26 on the underlying target vertebrae. The incisions 40 are then made along these lines. After the incisions are made, blunt finger dissection is carried through the soft tissues of the paraspinous musculature down to the dorsal surface of the facet joint. A routinely available Jamshidi bone biopsy needle and trocar (not shown) are then placed over the facet joint space under fluoroscopic guidance.

Figure 5:
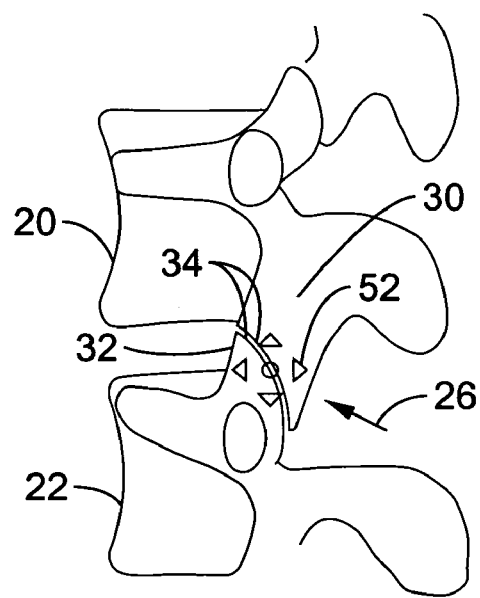
FIG. 5 is a view of the lumbar spine rotated to show the horizontal planes of the facet joint.

Referring now to FIG. 5, a television image intensifier fluoroscopic c-arm (not shown) is precisely aligned with the transverse plane of the superior end plate of the vertebrae, and then rolled in this plane, parallel to the superior vertebral end-plate, to the point where the planes of the subchondral surfaces 34 of the first facet joint 26 are visualized, i.e. "facet view." A radiolucent implant guide 50 may then be positioned at facet joint 26 to determine the size of the implant based on the patient's anatomy.

Generally, the larger the implant, the better the stress distribution on the facet joint articular processes. Therefore, the patient specific implant size is selected based on the largest configuration that can be accommodated by the bone mass of the articular processes 30, 32. As illustrated in FIG. 6A-B, implant guide 50 has a radiolucent marker 52 on a face plate 54 at the end of arm 56. When placed at the target facet joint 26, the marker 52 shows up clearly on image intensifier monitor screen to provide a reference as to the available workspace for the implant.

Referring now to FIG. 7, the biopsy needle may then be placed in the facet joint under fluoroscopic guidance. The obturator (not shown) in the center of the needle is removed and a thin stainless steel guide wire 60, e.g. K-wire, is placed in the facet joint 26. The guide wire 60 serves as a guide for surgical instruments and the introduction of the implant during the procedure. For example the guide wire 60 may by use in conjunction with a surgical kit including a range of size-specific drills, inserters, impactors, all cannulated to match to the internal diameter of the instrumentation system correlating to the outer diameter of the custom-length long K-wires 60.

Now referring to FIG. 8, a blunt-end soft-tissue dilator/guide 62, may then be positioned at the facet joint 26 by advancing it with fluoroscopic guidance over the guide wire 60 through the central cannula opening 64. The inside diameter $D_c$ of opening 64 is matched to guide wire diameter $D_g$ so that the blunt dilator 62 slides freely on the guide wire.

Referring to FIGS. 9A-B, the outside diameter of the blunt dilator $D_b$ is sized initially on the basis of preoperative planning by the surgeon, using a clear plastic overlay template 72 applied to the patient's x-ray, MRI or CT scan images 70. The template 72 has markings 74 which guide the surgeon's choice of the size of the dilator and implant, and is based on measurements of three dimensions of the combined articular processes 30, 32 surrounding the facet joint 26. The measurements may be confirmed intra-operatively with the radiolucent implant guide instrument 50 shown in FIGS. 5 and 6.

The blunt dilator 62 is preferably one of a kit of dilators comprising surgical stainless steel bodies having an outside diameter $D_b$ in increments of 4 mm, 6 mm, 8 mm and 10 mm.

The next step is to bore the bone path for implant. Two different systems have been developed for stabilizing the adjacent vertebrae: the ring implant embodied in FIGS. 10A through 14, and the dowel implant embodied in FIGS. 15 through 21. Because each system involves different preparation techniques, they will be described separately in detail below.

1. Ring Implant

FIGS. 10A-B illustrate two preferred embodiments 80, 96 of the ring implant. Referring now to FIG. 10A, ring implant 80 comprises a cylindrical tube with walls having thickness T, preferably composed of medical-grade metallic material, such as titanium, or a bioabsorbable material. The ring implant 80 has a plurality of fenestrations 84 to encourage growth of the cancellous bone surrounding and through the installed ring. The leading edge 90 of the implant has a taper 88 of diameter $D_t$ to facilitate entry into the circular scored bone defect produced by the drill.

The outer surface 82 may be roughened to create or enhance an immediate interference fit with the surrounding bone. For example, a plurality of protrusions 86 may be disposed on outer surface 82 to create an anchoring effect with the surrounding bone. In addition, the outer diameter $D_o$ of the ring implant may be oversized to create an interference fit with the surrounding bone. The ring implant may have a length ranging in 6 mm to 12 mm corresponding to the desired depth of the bored bone path. The outside diameter $D_o$ may range from 4 mm to 12 mm, also depending on the patient's measured anatomic geometry. The ring implant 80 may also be one of a kit of implants having increments of a 4 mm, 6 mm, 8 mm, 10 mm or 12 mm outside diameters and lengths of 6 mm, 8 mm, 10 mm or 12 mm.

Fenestrations 84 may be circular pathways as shown in FIG. 10A, or be configured to have one of a variety of shapes. For example, ring implant 96 illustrated in FIG. 10B, may comprise a plurality of columnar fenestrations 98 running axially along outer surface 82. Fenestrations 98 may also have raised edges 100 that create an interference fit with the surrounding bone. The ends of the columnar fenestrations preferably converge at tip 102. This axial configuration aides in guiding the implant 96 into the bone path while providing resistance to torque stresses across the articular processes spanned by the implant, effectively "locking" the facet joint.

As illustrated in FIG. 10C, showing a cross-section view through the middle of the ring implant 96, the implant 96 may also comprise a plurality of ridges 104 between each of the fenestrations 98. The ridges are highest at the middle of the band, and taper off toward the ends to form outer diameter 106. These ridges may also be repeated on the inner diameter of the ring to form an interference fit with the other side of the kerf (not shown). The "star-like" longitudinal orientation of the ridges 104 and fenestrations 98 not only facilitate the process of driving the implant into the bone, but also help resist rotational forces from twisting the ring in the implant, as the ridges 104 run perpendicular to the rotational moment created by the facet joint physiologic stress. The immediate interference fit of the implant is an important design feature which immobilizes the vertebral articulation allowing rapid ingrowth of new blood vessels which support the formation of the new bone which will biologically fuse the vertebrae together.

FIG. 10D illustrates a preferred embodiment without the raised edges at the openings of fenestrations 98. This configuration still provides ample rotational resistance and interference with the surrounding bone, while simplifying the configuration for ease of manufacture.

Referring to FIG. 11, hollow-core drill 110 having a wall thickness $T_d$ may be used to create a scored bone path or kerf for the implant. The drill 110 may have an inside diameter matching the outside diameter $D_b$ of the chosen dilator 62 so that the drill 110 may be positioned over and directed by the dilator 62. The outside diameter $D_{od}$ and wall thickness $T_d$ of the drill 110 are preferably sized to closely match the outside diameter $D_o$ and thickness T of the ring implant 80 or 96. For an interference fit, the outside diameter $D_{od}$ of the drill 110 may be configured to match the taper diameter $D_t$ of the implant 80.

A 'T'-handle 112 protruding 90° from the sides of the hollow core drill tube may also be included to allow the surgeon to hand drill the bone around the facet joint 26. Drill 110 may also be configured with an internal stop 116, such that a notch 114 on the dilator 62 acts to limit the depth of the drill to prevent penetration of the ventral aspect of the combined articular processes and possible injury to the underlying nerve root.

Now referring to FIG. 12, the drill 110 is advanced past the dilator 62 into the combined inferior articular process 30 and the superior articular process 32 to create a tubular bone path 120 comprising ring-shaped kerfs 122 and 124 in the respective articular processes. The bone path 120 is preferably drilled to a depth of approximately 75% of the depth of the facet joint bone mass. The drilling of kerfs 122, 124 leaves semi-circular bone protrusions 126, 128 at the opposing sides of the opposing subchondral surfaces 34.

Referring now to FIG. 13, drill 110 is removed and the ring implant 80 or 96 is driven into the bone path 120 via an impactor 140. Impactor 140 is shown in FIG. 14 in conjunction with slap hammer 144, dilator-guide 62 and guide wire 60 to press the ring implant 80, 96 into the scored bone. With the ring configuration, the fenestrations in the implant allow bone growth from the articular processes through the walls of the implant to the protrusions 126, 128. This has the effect of locking the implant 80, 96 in place and results in a stronger interface between the implant and the surrounding bone.

The ring implant configuration is intended to constrain the physiologic gliding motion of the facet joint 26 through a circumferential tension band effect. In doing so, it neutralizes the predominantly shear joint reactive forces imposed upon those small portions of the implant which cross the dense cortical bone surfaces underlying the facet joint 26 parallel articular surfaces 34.

Previously described facet joint fixation implants have, on the whole, failed due to their inability to neutralize the physiologic angulatory and rotational stresses between the adjacent vertebrae at the point where the implant crosses the dense cortical bone underlying the soft articular cartilage of the facet joint surfaces. Stresses applied to a spine fusion implant which exceed the local instant yield strength of the surrounding cortical bone, the strongest biologic component at such an interface, produce localized progressive loosening and failure of the fixation of the implant, disrupting the healing neovascularization essential for bone formation and leading to a non-union of the intended fusion of the motion segment.

With the ring implant 80, 96 of the present invention, joint reactive forces produced by physiologic loading of the lumbar spine are translated into compressive forces which are transmitted to the column of bone surrounding and encircled by the implant. Wolf's law is a statement of the bone-forming or osteogenic reaction of the cellular elements of bone when subjected to long-term compressive stress. The ring implant 80, 96 of the present invention maximizes the translation of the commonly occurring and potentially failure-producing focal, supraphysiologic stresses imposed upon the bone-implant interface into broad areas of compressive strain by stimulating peri-implant bone formation and enhanced biologic fixation.

With a tight immediate interference fit and progressive osteointegration of the ring implant, pull-out forces along the implant axis are effectively resisted, since the forces normally 'seen' by the implant along this axis are low.

After the ring implant 80, 96 is installed, the guide wire 60 is then removed from the patient. The procedure is then repeated on the opposing facet joint on the other side of the sagittal plane 42 to complete the immobilization of the adjacent vertebrae 20, 22.

It is appreciated that the system of the present invention will be used as a part of the spine surgeon's reconstructive armamentarium, and may be installed in conjunction with other posterior devices such as pedicle screws (not shown), to provide adjunctive stabilization after anterior spinal surgery such as placement of an anterior interbody implant, or as a minimally invasive salvage procedure following a failed previous attempt at spinal fusion. The implant system of the present invention will have broad utility in a number of other clinical situations where it is beneficial to neutralize the forces transmitted across the facet joints comprising the posterior-lateral intervertebral articulations. Examples of systems using pedicle screws are disclosed in U.S. Pat. Nos. 6,648,915; 6,010,503; 5,946,760; 5,863,293; 4,653,481, etc., the entire disclosures of which are incorporated herein by reference.

2. Dowel Implant

FIG. 15 illustrates a preferred embodiment of a dowel implant 200 in accordance with the present invention. Dowel implant 200 is relatively solid and intended to maximize an immediate interference fit between the roughened outer surface 202 of the implant and the trabeculae of the cancellous bone surrounding the joint to be fused. The implant body is preferably constructed of a porous biocompatible material conducive to bony ingrowth such as nitinol, sintered titanium, tantalum beads or similar material. The dowel implant has relatively central solid core to prevent implant deformation due to crush loading of the implant by the tamp during insertion.

In a preferred embodiment, the implant 200 may comprise or have disposed on the outer surface 202 tantalum beads 204 enhance more rapid bone ingrowth, in to or as an alternative to the tantalum beads 204, the implant may be plasma sprayed with calcium hydroxyapatite to further enhance bone ingrowth.

Preferably, dowel implant is tapered so that leading edge diameter $D_1$ is smaller than the trailing edge diameter $D_2$. Although a variety of taper dimensions may be used, the taper typically has a very shallow angle (e.g. 2-3 degrees), or a 0.1 cm diameter decrease per cm of length of the dowel to enhance the press-fit interdigitation between the material of the outer surface of the implant and the rough surrounding cancellous bone in order to resist 'back-out' failure of the implant along the insertional axis. The dowel implant 200 may be one of a kit of implants ranging in increments of in 6 mm, 8 mm, 10 mm and 12 mm outside diameters with lengths of 4 mm, 6 mm, 8 mm, and 10 mm.

The implant 200 is cannulated with an axial hole 206 having a diameter $D_c$ configured so that the implant can be advanced into place over guide wire 60.

There are a number of possible engineering variants of this basic implant design to optimize implant stability, implantation ease and manufacturing suitability. As illustrated in FIGS. 16A and 16B, dowel implants 210 may comprise axial ridges 214 on the outer surface to maximize resistance to torque-based failure modes. FIGS. 16C and 16D show an alternative dowel implant 208 with axial undulations 212 to resist torsional motion.

As with the ring implant, a template system such as that used in FIG. 9A-B may be used during the pre-operative planning process to assess the facet joint periarticular bone mass. With the assessed bone dimensions, the surgeon can determine the largest allowable implant for each facet joint 26. An intra-operative radiolucent sizing guide 50, may be advanced down k-wire 60 to facet joint 26 to affirm the preoperative assessment.

As illustrated in FIG. 17, a dowel drill 220 is advanced to the implant site at the facet joint 26. Drill 220 has a tapered thread 226 to cut the bone to accept the desired tapered dowel implant 200 diameter. The drill 200 preferably has a 'T'-handle 224 protruding 90° from the sides of the drill tube to allow the surgeon to hand drill the bone around the facet joint 26. The drill may also be configured with a positive stop to prevent over-penetration into the bone and potential injury to the underlying nerve root. The drill 220 is preferably cannulated with axial hole 222 so that the drill may be advanced over guide wire 60 to the implant site.

Now referring to FIG. 18, the drill 220 is advanced into the inferior articular process 30 and the superior articular process 32 to create a tapered cylindrical bone path 230 resulting in semi-circular grooves 232 and 234 into opposing subchondral surfaces 34.

As illustrated in FIG. 19, drill 220 is removed and the dowel implant 200 is driven into the bone path 230 over dilator-guide 242 via impactor 240. Once pressed into place, the interference fit of the dowel and the surrounding bone of articular processes 30 and 32 lock the dowel into place, as illustrated in top sectional view in FIG. 20 and posterior-lateral view in FIG. 21.

The dowel implant 200 is designed to compress and interdigitate with the surrounding cancellous bone of bore 230 as it is tapped into place. The installed implant provides a mechanical lock of the facet joint articular surfaces, resisting shear forces across the joint with the maximum compressive strength of the metal at the mid-cross sectional dimension of the dowel 200. The circumferential interdigitation of the implant outer surface 202 with the spicules of the surrounding cancellous bone provide the necessary stability to protect the bone-implant interface from failure due to applied torque or bending moments.

In addition to the ring and dowel implants discussed above, different shaped implants such as a cruciate self-cutting staple implant(not shown) may also be employed. However, the ring and dowel systems appear to have advantages in ease of fabrication, safety and stability.

It is anticipated that as a result of the minimally traumatic, tissue sparing nature of the facet fusion system of the present invention, many patients will be able to undergo posterior spinal fusion surgery in an outpatient setting, dramatically reducing the cost and potential morbidity of a hospital stay. Patients will generally be placed into a polypropylene trunk orthosis after surgery and are encouraged to ambulate. The progress of the patient's fusion is followed with radiographs in the surgeon's office. The preferable materials for fabrication of the implants, such as tantalum, titanium, nitinol, or a bioabsorbable polymer, are compatible with further diagnostic studies using the high magnetic field of an MRI scanner.

3. Training Aid

Referring to FIG. 22, the Image Guided Spine Surgical Training Device,™ or Visualizer™ 300 may be used in conjunction with the above disclosed systems and methods in the operating room to refresh the surgeon's visualization of the path of the instrumentation and to enhance the surgeon's review of the essential fluoroscopic views with the x-ray technician who will operate and repeatedly reposition the c-arm during the procedure. With a sterilely draped, anesthetized patient in the prone position on the radiolucent operating table, the precise positioning of the C-arm or image intensifier is the only method by which adequate visualization of the complex three dimensional anatomy of the lumbar spine will be obtained during the procedure. A pre-operative review of the procedure using the training aid 300 with the operative team adds significantly to the safety and reproducibility of images necessary for the technically demanding task of image-guided spine surgery. The training device 300 may be first introduced during the initial surgeon training course in use of the FacetLock™ system and is also useful as a tool to review the visualization necessary for many of the current minimally invasive lumbar spinal procedures which depend upon fluoroscopic guidance. The three dimensional perspective and highlighted anatomic cues of the training aid are also depicted on an accompanying computer graphics program which allows the surgeon to access the vertebral references on a computer or via the internet.

The training device 300 generally comprises a plurality of simulated vertebrae 304 strung along support wire 306 that is attached to base 302. The vertebrae 304 are separated by spacers 310 and kept on the threaded support 306 via nuts 308. Each of the vertebrae 304 have color coded regions 312 and 314 to guide the surgeon and the fluoroscopic technician through the steps to achieve precise reproducible visualization of each individual vertebra with the repeated changes of position of the c-arm during the case. The surgical technique for the procedure relies on a rapid, absolutely reproducible step-by-step positioning of the c-arm in three dimensions for each of four views necessary to place spine instrumentation. The colored areas 312 and 314 of the training device 300 highlight what the surgeon and the technician should look for as a target at each step of the process of positioning the fluoroscope in reference to vertebral anatomy while progressively increasing the precision of the alignment and refining the reproducibility of the visualization for the operating surgeon.

During initial surgeon training courses, special colored glass crayons may be used in conjunction with the training aid 300 to draw on the fluoroscope screen to emphasize the radiographic anatomical points used for reference. The colors of the markers preferably match the colored regions 312, 314 of the model 300 to enhance the process of visual learning. If necessary, the manufacturer's representative present in the operating room may use the markers during surgical cases to assist the surgeon and fluoroscopic technician with technical tips and hints. Additionally, the surgeon may use the training aid 300 in the office for patient education purposes. The Visualizer™ training aid 30 is a powerful marketing tool for the instrumentation system and should significantly enhance surgeon adoption of this procedure and minimally invasive image-guided spinal surgery in general.

FIG. 23 illustrates a top view of a horizontal section of an individual vertebral segment model 304 of the training aid 300 taken just above the junction of the pedicles 320. Conical bores 328 and 330 demonstrate the anatomic positioning cues and safe pathways for minimally invasive fluoroscopically guided vertebral instrumentation. Anterior bore 328 comprises a conical path forming an anterior hole 324 on the anterior portion of the vertebra body 326 converging toward the pedicle 320, and connecting with posterior bore 330, which diverges outward from the pedicle 320 to form a posterior hole 322. Internal bore surface region 332 may be color-coded for illustration.

FIG. 24 illustrates a left side view of the lateral aspect of a single vertebral model segment 304. The anterior margin 334 of the opening 324 may also be color coded, e.g. with a brilliant red ring at its edge, to emphasize the anatomic dangers immediately anterior to the curved plane at the anterior-lateral boundary of the vertebra which is not evident in standard fluoroscopic views. The outer ring 336 on the top of the vertebral body 326 may be color coded to provide a reference plane for rotation about axis 342. To provide further reference of rotation along axis 342, upper saddle regions 338 on the upper surface of pedicles 320 may be color coded as well. To provide reference of rotation about vertical axis 344, regions 340 along the posterior ridges of the body 336 may be color coded.

FIG. 25 illustrates a posterior view of a segment 304 of the training aid. A posterior section 346 of the spinous process may be color-coded as a positioning reference in relation to the pedicles 322 for "roll" alignment about the longitudinal axis and within the horizontal plane of the superior endplate of the verteba 336. The starting point for pedicle cannulation 322 can be seen out of alignment with the anterior opening 324.

FIG. 26 shows an oblique view of the posterior-lateral aspect of the vertebral segment 304 in which the viewer's eye is precisely lined up with the axis of the central pathway formed by bores 328 and 330 through the pedicle 320 into the vertebral body 326. It is this view in which the training aid most dramatically illustrates the critical nature of a precise safe path for vertebral pedicle cannulation since the pedicle is surrounded on all four surfaces with spinal nerves and dura—the covering over the spinal nerves. The steps necessary to reproduce this position with the training aid provides a simulation of the steps necessary to achieve a perfect fluoroscopic positioning necessary for the intraoperative visualization of the pedicular axis, defining the center of the locus of safe paths for instrumentation through the pedicle 326 and relationships to adjacent 'at risk' structures. Holding the training aid vertebral segment 324 up to one eye with the other eye closed reproduces what will be seen on the fluoroscopic monitor and allows the viewer to move the model slightly and visualize the changing relationships between the anatomic landmarks on the vertebra and the desired instrument trajectory which will only be seen in two dimensions on the fluoroscopic monitor during surgery.

Figure 27A:
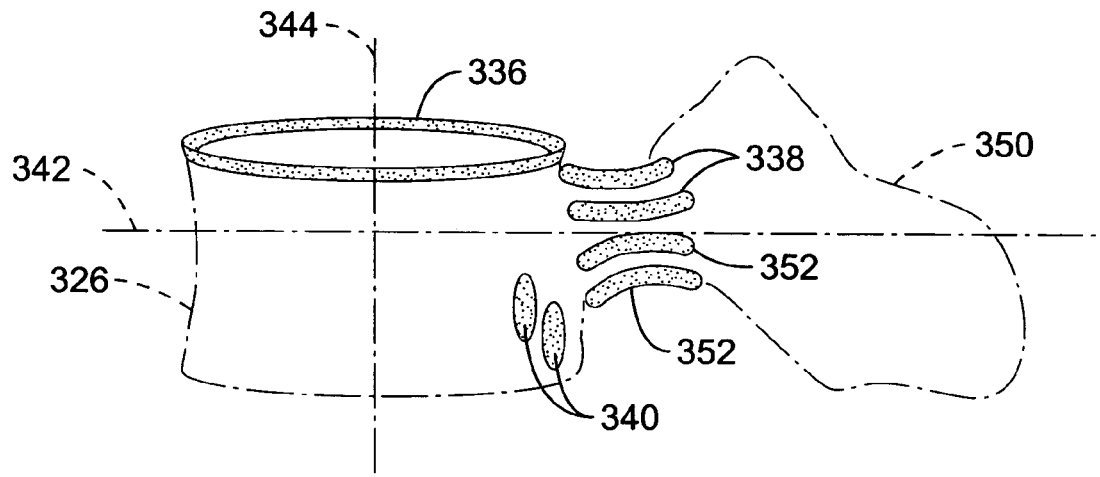

FIGS. 27A-D illustrate the color coded training aid landmarks with reference to a representative image that would show up on a fluoroscopic monitor. FIG. 27A demonstrates the effects of slight fluoroscopic rotational mal-positioning about the longitudinal 342 and vertical 344 axes of the vertebral model 304, showing loss of alignment of the highlighted anatomic areas on the model which correspond to similar details on the fluoroscopic image which will be seen intraoperatively. For example, rotation out of the horizontal plane in the longitudinal axis shows an ellipse for marked region 336 on the top of the body 326, and multiple lines for each of the marked upper saddle region 338 and lower saddle regions 352. Rotation in the vertical axis 344 show to marks for posterior ridge regions 340.

Figure 27B:
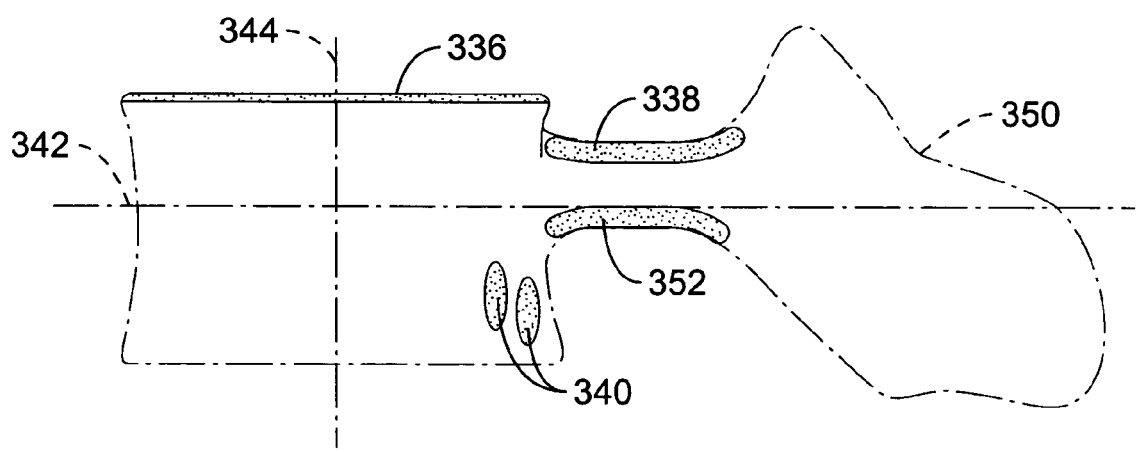

FIG. 27B demonstrates the next step in fluoroscopic c-arm alignment of the reference points on the training aid 304 necessary to produce an ideal lateral fluoroscopic image of the vertebral body. Upper region marking 336, which is the horizontal plane of the superior endplate, should show up as a single line, and the upper and lower saddle regions 338 and 352 also show up as single superimposed arched lines. In this illustration there is slight fluoroscope mal-alignment around the longitudinal axis 342 which is illustrated by the lack of alignment of the anatomic regions 340 highlighted on the posteriolateral columns of the vertebral body 326.

Figure 27C:
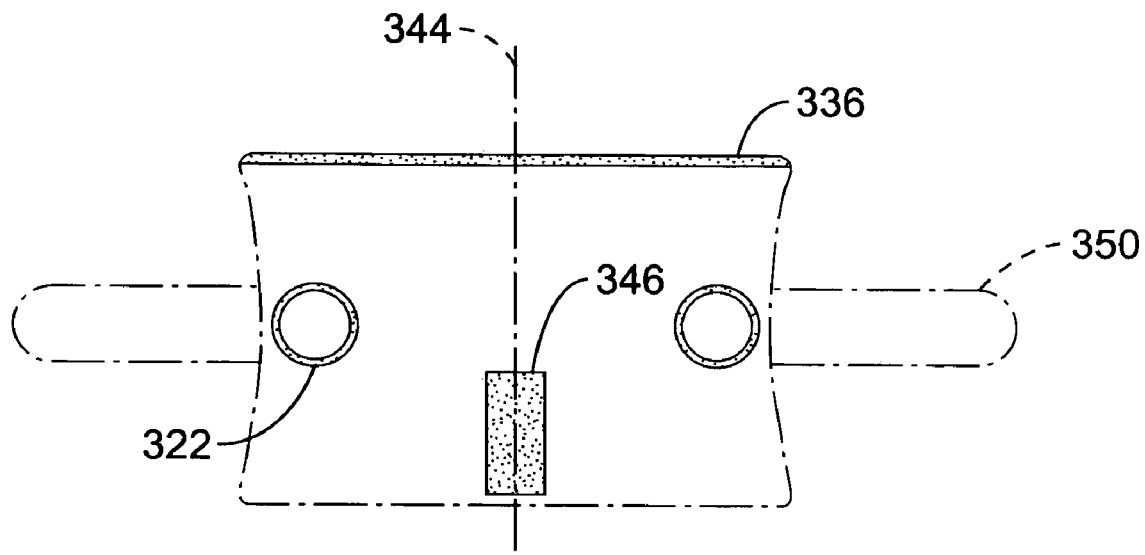

FIG. 27C shows the posterior view of the vertebra segment 304 with the posterior spinal process region 346 lined up in a position equidistant between the two pedicle cortical rings 322 and in the plane of the superior vertebral end plate which is seen as a single line 336. This true anterior-posterior view provides an important initial alignment of the fluoroscopic in reference to the vertebra.

Figure 27D:
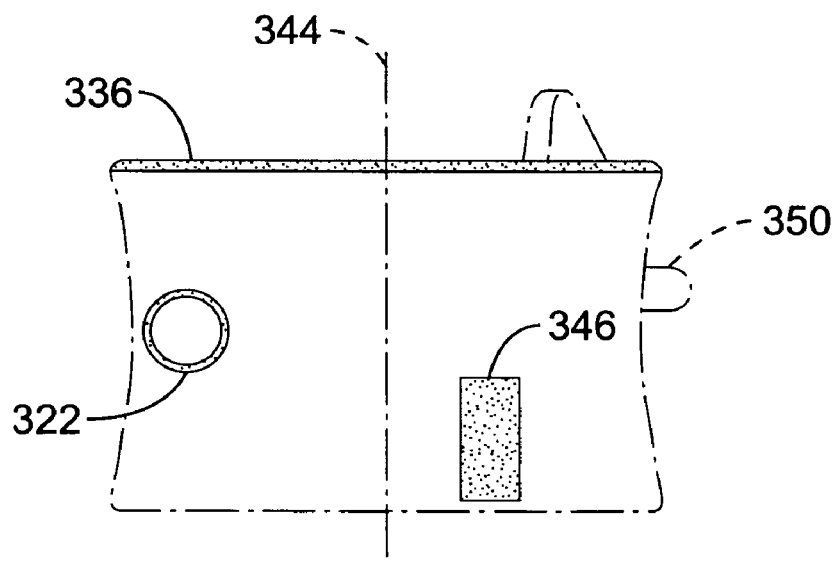

As illustrated in FIG. 27D, the fluoroscope position or the vertebra section of the training aid may be rotated about vertical axis 344 in the plane of the superior vertebral end plate 336 to precisely line up with the axis of the central pedicle instrumentation pathway formed by bores 328 and 330, and posterior hole 322. It is in this view that guidance for the skin incisions is obtained and the percutaneous instrumentation of the vertebral body through the pedicle will be performed.

In alternative embodiment, the three dimensional vertebral anatomy and distinctive color coded regions of the training aid are reproduced in a three dimensional graphic computer program which is used during initial surgeon training and as a refresher for pre-operative review of the technique and relevant fluoroscopic anatomy. The program, which allows three axis manipulation of the fluoroscopic perspective of the vertebral anatomy, may be given to surgeons completing training, and may be accessible through the internet from a central server and may be used in patient educational and promotional materials.

The color-coded, clear step-wise techniques for the positioning of the fluoroscope, combined with the clear image of the geometry of the highlighted sections of the training aid creates a reproducible approach to the complex vertebral anatomy with maximum safety for the delicate structures which lie close to the surgical approach on all sides.

Although the description above contains many details, these should not be construed as limiting the scope of the invention but as merely providing illustrations of some of the presently preferred embodiments of this invention. For example, the underlying biomechanical principles of the system and methods of the present invention have a potentially much broader applicability, and may be applied at larger scales to the clinical problems of fusion of other joints such as the ankle, wrist, and other joints of large radius of joint curvature. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for stabilizing adjacent vertebrae of the spine, the adjacent vertebrae comprising superior and inferior articular processes having opposing subchondral articular surfaces to form first and second bilateral posterior facet joints, the method comprising:
    forming a bone path into the subchondral bone of the articular surfaces of the first facet joint;
    installing an implant axially into the bone path of the first facet joint; and
    immobilizing the first facet joint of the articulation between the adjacent vertebrae;
    wherein the implant comprises one or more longitudinal ridges that extend at least along a portion of the length of the implant;
    wherein, when the implant is being installed into the bone path, the one or more longitudinal ridges create one or more longitudinal grooves that extend radially into the bone of the preformed bone path and axially along the preformed bone path;
    wherein, when the implant is installed, the one or more longitudinal ridges are in intimate contact with the longitudinal groove created by it along at least a portion of the length of the bone path to inhibit rotation of the implant within the bone path.

2. A method as recited in claim 1, further comprising:
    forming a path into the subchondral bone of the articular surfaces of the second facet joint; and
    installing an implant into the bone path of the second facet joint;
    wherein the implant is configured to immobilize the second facet joint of the articulation between the adjacent vertebrae.

3. A method as recited in claim 1, wherein forming a path into the subchondral bone comprises:
    drilling a cylindrical bore into the subchondral articular surfaces;
    wherein a portion of each subchondral articular surface is removed to form grooves defining opposite ends of the cylindrical bore.

4. A method as recited in claim 3, wherein the cylindrical bore is drilled in a path substantially parallel to the planes of the subchondral surfaces.

5. A method as recited in claim 3, wherein the bone is drilled to have a diameter that tapers to a smaller diameter inward into the bore,
    wherein installing an implant comprises driving an oversized dowel into the scored bone path to create an interference fit with opposing first and second vertebrae to mechanically lock the articulation of the first facet joint; and
    wherein the oversized dowel has a taper substantially matching the taper of the bone path.

6. A method as recited in claim 5, wherein the implant comprises a roughened surface to promote bony ingrowth into the implant.

7. A method as recited in claim 1, wherein the method is performed percutaneously under fluoroscopic guidance.

8. A method as recited in claim 7, wherein forming a path into the subchondral bone comprises:
    visualizing the planes of the subchondral surfaces of the facet joint; determining the size of the path into the subchondral bone according to said visualization of the facet joint;
    installing a blunt dilator down to an outer surface of the facet joint; and
    drilling a cylindrical bore into the opposing articular processes, the blunt dilator guiding the path of the cylindrical bore.

9. A method as recited in claim 8, wherein drilling a cylindrical bore comprises advancing a hollow-core drill having an inside diameter closely matching the outside diameter of the dilator over the dilator to score kerfs into the opposing articular processes.

10. A method as recited in claim 9, wherein installing an implant comprises driving a ring implant into the cylindrical kerfs formed in the articular processes;
    the ring implant constraining motion of the facet joint through circumferential tension band effect.

11. A method as recited in claim 9, wherein the dilator is configured to limit the depth of the bored bone path.

12. A method as recited in claim 11, wherein the bone path is drilled to a depth corresponding to approximately 75% of the facet joint bone mass.

13. A method as recited in claim 8, wherein visualizing the planes of the subchondral surfaces of the facet joint is done fluoroscopically.

14. A method as recited in claim 13, wherein determining the size of the bone path comprises positioning a radiolucent implant guide at the facet joint and comparing the implant guide against bone mass of the articular processes.

15. A method as recited in claim 14, further comprising installing a guide wire into the facet joint.

16. A method as recited in claim 15, wherein the blunt dilator is positioned at the facet joint by advancing it over the guide wire.

17. A method as recited in claim 15, wherein a radiolucent implant guide is positioned at the facet joint to measure the size of the bone path.

18. A method as recited in claim 1, wherein the bore is drilled from a dorsal aspect of the facet joint.

19. A method as recited in claim 1, wherein the bore is drilled from a dorsal aspect of the facet joint toward a ventral aspect of the facet joint.

20. A method as recited in claim 1, wherein the one or more longitudinal ridges are installed substantially perpendicular to the rotational moment created by the facet joint physiologic stress.

21. A method as recited in claim 1, wherein the one or more longitudinal ridges engage the bone path at a location at least along the distal half of the bone path.

22. A method as recited in claim 1:
   wherein the implant comprises a plurality of longitudinal fenestrations disposed substantially parallel to the one or more longitudinal ridges;
   wherein the longitudinal fenestrations promote bony ingrowth from the bone path radially inward into the implant to fuse the facet joint.

23. A method for stabilizing adjacent vertebrae of the spine, the adjacent vertebrae comprising superior and inferior articular processes having opposing subchondral articular surfaces to form first and second bilateral posterior facet joints, the method comprising:
   forming a bone path into the subchondral bone of the articular surfaces of the first facet joint;
   guiding an implant axially into the bone path of the first facet joint;
   the implant having a diameter correlating to a diameter of the bone path such that the implant creates an interference fit with the bone path when installed in the bone path;
   wherein the implant comprises one or more longitudinal ridges that extend axially at least along a portion of the length of the implant;
   the one or more longitudinal ridges extending radially from the diameter of the implant such that the one or more longitudinal ridges extend radially into the bone of the bone path as the implant is guided into the path;
   wherein, when installed, the one or more longitudinal ridges are in intimate contact with bone surrounding the one or more longitudinal ridges for at least a portion of the length of the bone path to inhibit rotation of the implant within the bone path; and
   immobilizing the first facet joint of the articulation between the adjacent vertebrae against translational and rotational forces imposed on the first facet joint.

24. A method as recited in claim 23, further comprising:
   promoting bony ingrowth radially into the implant from the bored bone path to fuse the first facet joint.

25. A method as recited in claim 23, wherein the one or more longitudinal ridges are positioned on the implant such that the implant is guided axially into the bone path without rotation of the implant with respect to the bone path.

* * * * *